United States Patent
Hirai et al.

(10) Patent No.: US 9,012,619 B2
(45) Date of Patent: Apr. 21, 2015

(54) PROBE FOR DETECTING ABL GENE MUTATION AND USES THEREOF

(75) Inventors: Mitsuharu Hirai, Kyoto (JP); Satoshi Majima, Kyoto (JP); Taira Maekawa, Kyoto (JP); Shinya Kimura, Kyoto (JP)

(73) Assignee: Arkray, Inc., Kyoto (JP)

( * ) Notice: Subject to any disclaimer, the term of this patent is extended or adjusted under 35 U.S.C. 154(b) by 318 days.

(21) Appl. No.: 12/293,916

(22) PCT Filed: Feb. 19, 2008

(86) PCT No.: PCT/JP2008/052732
§ 371 (c)(1),
(2), (4) Date: Sep. 22, 2008

(87) PCT Pub. No.: WO2008/102760
PCT Pub. Date: Aug. 28, 2008

(65) Prior Publication Data
US 2009/0176231 A1      Jul. 9, 2009

(30) Foreign Application Priority Data

Feb. 20, 2007   (JP) ................................. 2007-040077

(51) Int. Cl.
*C12Q 1/68* (2006.01)
*C07H 21/04* (2006.01)

(52) U.S. Cl.
CPC ......... *C12Q 1/6886* (2013.01); *C12Q 2600/172* (2013.01)

(58) Field of Classification Search
CPC ....................... C12Q 1/6886; C12Q 2600/172
See application file for complete search history.

(56) References Cited

U.S. PATENT DOCUMENTS

| 6,174,670 B1 * | 1/2001 | Wittwer et al. ................... 435/6 |
| 2006/0269956 A1 | 11/2006 | Sawyers et al. | |

FOREIGN PATENT DOCUMENTS

| EP | 1715063 A2 | 10/2006 |
| JP | 2003-528626 A | 9/2003 |
| JP | 2004-537992 A | 12/2004 |
| WO | WO 01/73118 A2 | 10/2001 |
| WO | WO 02/102976 A2 | 12/2002 |
| WO | 2004-97209 A | 4/2004 |
| WO | WO 2007/055244 A1 | 5/2007 |
| WO | WO 2008/018305 A1 | 2/2008 |

OTHER PUBLICATIONS

Genbank Accession XM_001357959 GI:125773474.*
Hochhaus et al (Leukemia (2002) vol. 16, pp. 2190-2196).*
GenBank Accession No. NM_005157.3 GI:62362413 (Apr. 7, 2005).*
Schutz et al (Biotechniques (1999) 1219-1221 and 1224).*
Wittwer (Analytical Biochemistry (2001) vol. 290, pp. 89-97).*
Escara et al (biopolymers (1980) vol. 19, pp. 1315-1320).*
Undenfriende et al (Analytical biochemistry (1692) vol. 3, pp. 49-59).*
International Search Report of PCT/JP2008/052732, dated Mar. 25, 2008.
Heinrich et al. "A Novel, High-Throughput Assay for Detection of ABL T3151 Mutations." Blood: American Society of Hematology annual meeting abstracts, Abstract 2334, 2006.
Steensma "JAK2 V617F in Myeloid Disorders: Molecular Diagnostic Techniques and Their Clinical Utility." Journal of Molecular Diagnostics, vol. 8(4), Sep. 2006, pp. 397-411.
Soverini et al. "Denaturing-HPLC-Based Assay for Detection of ABL Mutations in Chronic Myeloid Leukemia Patients Resistant to Imatinib." Clinical Chemistry, vol. 50(7), 2004, pp. 1205-1213.
Gorre et al. (2001) Clinical resistance to STI-571 cancer therapy caused by BCR-ABL gene mutation or amplification, Science 293:876-880.
Hughes et al. (2006) Monitoring CML patients responding to treatment with tyrosine kinase inhibitors: review and recommendations for harmonizing current methodology for detecting BCR-ABL transcripts and kinase domain mutations and for expressing results, Blood 108:28-37.
Kreuzer et al. (2003) Preexistence and evolution of imatinib mesylate-resistant clones in chronic myelogenous leukemia detected by a PNA-based PCR clamping technique, Ann. Hematol. 82:284-289.
Soverini et al. (2006) Contribution of ABL kinase domain mutations to imatinib resistance in different subsets of philadelphia-positive patients: by the GIMEMA working party on chronic lyeloid leukemia, Clin. Cancer Res. 12:7374-7379.
Bradeen et al., "Comparison of imatinib mesylate, dasatinib (BMS-354825), and nilotinib (AMN107) in an N-ethyl-N-nitrosourea (ENU)-based mutagenesis screen: high efficacy of drug combinations," Blood, 108: 2332-2338 (2006).
Capitani et al., "The Bcl-2 Family as a Rational Target for the Treatment of B-Cell Chronic Lymphocytic Leukaemia," Current Medicinal Chemistry, 17: 801-811 (2010).
Gora-Tybor et al., "Targeted Drugs in Chronic Myeloid Leukemia," Current Medicinal Chemistry, 15: 3036-3051 (2008).
Extended European Search Report dated Dec. 22, 2010, European Patent Application No. 8711556.4.
Office Action dated Nov. 24, 2010, with partial English Translation, Korean Patent Application No. 10-2008-7021617.

* cited by examiner

*Primary Examiner* — Steven Pohnert
(74) *Attorney, Agent, or Firm* — Morgan, Lewis & Bockius LLP

(57) ABSTRACT

Detection probes are provided that are capable of detecting a sequence to be detected containing a mutation even when a sequence not to be detected containing no mutation coexists with the sequence to be detected containing a mutation, which are different only in a single base from each other. At least one oligonucleotide selected from the group consisting of SEQ ID NOs: 2~16 is used as a probe. Even in a sample containing an abl gene in which a mutation has occurred and an abl gene in which no mutation has occurred, the use of such probes in, for example, Tm analysis allows the mutation to be detected.

12 Claims, 8 Drawing Sheets

SEQUENCE LISTING

<160> NUMBER OF SEQ ID NOS: 50

<210> SEQ ID NO 1
<211> LENGTH: 5381
<212> TYPE: DNA
<213> ORGANISM: Homo sapiens

<400> SEQUENCE: 1

```
atgttggaga tctgcctgaa gctggtgggc tgcaaatcca agaaggggct gtcctcgtcc      60
tccagctgtt atctggaaga agcccttcag cggccagtag catctgactt tgagcctcag     120
ggtctgagtg aagccgctcg ttggaactcc aaggaaaacc ttctcgctgg acccagtgaa     180
aatgacccca acctttcgt tgcactgtat gattttgtgg ccagtggaga taacactcta      240
agcataacta aaggtgaaaa gctccgggtc ttaggctata atcacaatgg ggaatggtgt     300
gaagcccaaa ccaaaaatgg ccaaggctgg gtcccaagca actacatcac gccagtcaac     360
agtctggaga aacactcctg gtaccatggg cctgtgtccc gcaatgccgc tgagtatctg     420
ctgagcagcg ggatcaatgg cagcttcttg gtgcgtgaga gtgagagcag tcctggccag     480
aggtccatct cgctgagata cgaagggagg gtgtaccatt acaggatcaa cactgcttct     540
gatggcaagc tctacgtctc ctccgagagc cgcttcaaca ccctggccga gttggttcat     600
catcattcaa cggtggccga cgggctcatc accacgctcc attatccagc cccaaagcgc     660
aacaagccca ctgtctatgg tgtgtccccc aactacgaca agtgggagat ggaacgcacg     720
gacatcacca tgaagcacaa gctgggcggg ggccagtacg gggaggtgta cgagggcgtg     780
tggaagaaat acagcctgac ggtggccgtg aagaccttga aggaggacac catggaggtg     840
gaagagttct tgaaagaagc tgcagtcatg aaagagatca acacccctaa cctggtgcag     900
ctccttgggg tctgcacccg ggagccccg ttctatatca tcactgagtt catgacctac      960
gggaacctcc tggactacct gagggagtgc aaccggcagg aggtgaacgc cgtggtgctg    1020
ctgtacatgg ccactcagat ctcgtcagcc atggagtacc tggagaagaa aaacttcatc    1080
cacagagatc ttgctgcccg aaactgcctg gtaggggaga accacttggt gaaggtagct    1140 gatttttggcc tgagcaggtt gatgacaggg gacacctaca cagcccatgc tggagccaag    1200
ttccccatca aatggactgc acccgagagc ctggcctaca acaagttctc catcaagtcc    1260
gacgtctggg catttggagt attgctttgg gaaattgcta cctatggcat gtcccttac     1320 ccgggaattg acctgtccca ggtgtatgag ctgctagaga aggactaccg catggagcgc    1380
```

```
ccagaaggct gcccagagaa ggtctatgaa ctcatgcgag catgttggca gtggaatccc   1440
tctgaccggc cctcctttgc tgaaatccac caagcctttg aaacaatgtt ccaggaatcc   1500
agtatctcag acgaagtgga aaaggagctg gggaaacaag gcgtccgtgg ggctgtgagt   1560
accttgctgc aggccccaga gctgccacc aagacgagga cctccaggag agctgcagag   1620
cacagagaca ccactgacgt gcctgagatg cctcactcca agggccaggg agagagcgat   1680
cctctggacc atgagcctgc cgtgtctcca ttgctccctc gaaaagagcg aggtcccccg   1740
gagggcggcc tgaatgaaga tgagcgcctt ctccccaaag acaaaaagac caacttgttc   1800
agcgccttga tcaagaagaa gaagaagaca gccccaaccc ctcccaaacg cagcagctcc   1860
ttccgggaga tggacggcca gccggagcgc agaggggccg gcgaggaaga gggccgagac   1920
atcagcaacg gggcactggc tttcaccccc ttggacacag ctgacccagc caagtcccca   1980
aagcccagca atgggctgg ggtccccaat ggagccctcc gggagtccgg gggctcaggc   2040
ttccggtctc cccacctgtg gaagaagtcc agcacgctga ccagcagccg cctagccacc   2100
ggcgaggagg agggcggtgg cagctccagc aagcgcttcc tgcgctcttg ctccgcctcc   2160
tgcgttcccc atgggccaa ggacacggag tggaggtcag tcacgctgcc tcgggacttg   2220
cagtccacgg gaagacagtt tgactcgtcc acatttggag gcacaaaag tgagaagccg   2280 gctctgcctc ggaagagggc aggggagaac aggtctgacc aggtgacccg aggcacagta   2340
acgcctcccc ccaggctggt gaaaaagaat gaggaagctg ctgatgaggt cttcaaagac   2400
atcatggagt ccagcccggg ctccagcccg cccaacctga ctccaaaacc cctccggcgg   2460
caggtcaccg tggcccctgc ctcgggcctc ccccacaagg aagaagctgg aaagggcagt   2520
gccttaggga cccctgctgc agctgagcca gtgaccccca ccagcaaagc aggctcaggt   2580
gcaccagggg gcaccagcaa gggccccgcc gaggagtcca gagtgaggag cacaagcac   2640 tcctctgagt cgccagggag ggacaagggg aaattgtcca ggctcaaacc tgccccgccg   2700
cccccaccag cagcctctgc agggaaggct ggaggaaagc cctcgcagag cccgagccag   2760
gaggcggccg ggaggcagt cctgggcgca aagacaaaag ccacgagtct ggttgatgct   2820
gtgaacagtg acgctgccaa gcccagccag ccgggagagg gcctcaaaaa gcccgtgctc   2880
ccggccactc caaagccaca gtccgccaag ccgtcgggga cccccatcag cccagccccc   2940
gttccctcca cgttgccatc agcatcctcg gccctggcag ggaccagcc gtcttccacc   3000 gccttcatcc ctctcatatc aacccgagtg tctcttcgga aaacccgcca gcctccagag   3060
cggatcgcca gcggcgccat caccaagggc gtggtcctgg acagcaccga ggcgctgtgc   3120
ctcgccatct ctaggaactc cgagcagatg gccagccaca gcgcagtgct ggaggccggc   3180
aaaaacctct acacgttctg cgtgagctat gtggattcca tccagcaaat gaggaacaag   3240
tttgccttcc gagaggccat caacaaactg gagaataatc tccgggagct tcagatctgc   3300
ccggcgacag caggcagtgg tccagcgcc actcaggact tcagcaagct cctcagttcg   3360
gtgaaggaaa tcagtgacat agtgcagagg tagcagcagt caggggtcag gtgtcaggcc   3420
cgtcggagct gcctgcagca catgcgggct cgcccatacc cgtgacagtg gctgacaagg   3480
gactagtgag tcagcaccctt ggcccaggag ctctgcgcca ggcagagctg agggccctgt   3540
ggagtccagc tctactacct acgtttgcac cgcctgccct cccgcacctt cctcctcccc   3600
gctccgtctc tgtcctcgaa ttttatctgt ggagttcctg ctccgtggac tgcagtcggc   3660
atgccaggac ccgccagccc cgctcccacc tagtgcccca gactgagctc tccaggccag   3720
```

```
gtgggaacgg ctgatgtgga ctgtcttttt cattttttc tctctggagc ccctcctccc       3780
ccggctgggc ctccttcttc cacttctcca agaatggaag cctgaactga ggccttgtgt       3840
gtcaggccct ctgcctgcac tccctggcct tgcccgtcgt gtgctgaaga catgtttcaa       3900
gaaccgcatt tcgggaaggg catgcacggg catgcacacg gctggtcact ctgccctctg       3960
ctgctgcccg gggtggggtg cactcgccat ttcctcacgt gcaggacagc tcttgatttg       4020
ggtggaaaac agggtgctaa agccaaccag cctttgggtc ctgggcaggt gggagctgaa       4080
aaggatcgag gcatggggca tgtcctttcc atctgtccac atccccagag cccagctctt       4140
gctctcttgt gacgtgcact gtgaatcctg gcaagaaagc ttgagtctca agggtggcag       4200
gtcactgtca ctgccgacat ccctccccca gcagaatgga ggcaggggac aagggaggca       4260
gtggctagtg gggtgaacag ctggtgccaa atagccccag actgggccca ggcaggtctg       4320
caagggccca gagtgaaccg tcctttcaca catctgggtg ccctgaaagg gcccttcccc       4380
tcccccactc ctctaagaca aagtagattc ttacaaggcc cttccttg gaacaagaca         4440 gccttcactt ttctgagttc ttgaagcatt tcaaagccct gcctctgtgt agccgccctg       4500
agagagaata gagctgccac tgggcacctg cgcacaggtg ggaggaaagg gcctggccag       4560
tcctggtcct ggctgcactc ttgaactggg cgaatgtctt atttaattac cgtgagtgac       4620
atagcctcat gttctgtggg ggtcatcagg gagggttagg aaaaccacaa acggagcccc       4680
tgaaagcctc acgtatttca cagagcacgc ctgccatctt ctccccgagg ctgccccagg       4740
ccggagccca gatacggggg ctgtgactct gggcagggac ccggggtctc ctggaccttg       4800
acagagcagc taactccgag agcagtgggc aggtggccgc ccctgaggct tcacgccggg       4860
agaagccacc ttcccacccc ttcataccgc ctcgtgccag cagcctcgca caggccctag       4920
ctttacgctc atcacctaaa cttgtacttt attttctga tagaaatggt ttcctctgga        4980 tcgtttatg cggttcttac agcacatcac ctctttgccc ccgacggctg tgacgcagcc        5040
ggagggaggc actagtcacc gacagcggcc ttgaagacag agcaaagcgc ccacccaggt       5100
cccccgactg cctgtctcca tgaggtactg gtcccttcct tttgttaacg tgatgtgcca      5160
ctatatttta cacgtatctc ttggtatgca tcttttatag acgctctttt ctaagtggcg       5220
tgtgcatagc gtcctgccct gcccctcgg gggcctgtgg tggctccccc tctgcttctc        5280
ggggtccagt gcattttgtt tctgtatatg attctctgtg gttttttttg aatccaaatc      5340
tgtcctctgt agtattttt aaataaatca gtgtttacat t                           5381

<210> SEQ ID NO 2
<211> LENGTH: 20
<212> TYPE: DNA
<213> ORGANISM: Artificial
<220> FEATURE:
<223> OTHER INFORMATION: probe

<400> SEQUENCE: 2
tgtgcttcac ggtgatgtcc                                                    20

<210> SEQ ID NO 3
<211> LENGTH: 28
<212> TYPE: DNA
<213> ORGANISM: Artificial
<220> FEATURE:
<223> OTHER INFORMATION: probe

<400> SEQUENCE: 3
gtgcttcacg gtgatgtccg tgcgttcc                                           28
```

<210> SEQ ID NO 4
<211> LENGTH: 17
<212> TYPE: DNA
<213> ORGANISM: Artificial
<220> FEATURE:
<223> OTHER INFORMATION: probe

<400> SEQUENCE: 4
caagctgggc gagggcc                                                  17

<210> SEQ ID NO 5
<211> LENGTH: 17
<212> TYPE: DNA
<213> ORGANISM: Artificial
<220> FEATURE:
<223> OTHER INFORMATION: probe

<400> SEQUENCE: 5
cacaagctgg gcgaggg                                                  17

<210> SEQ ID NO 6
<211> LENGTH: 21
<212> TYPE: DNA
<213> ORGANISM: Artificial
<220> FEATURE:
<223> OTHER INFORMATION: probe

<400> SEQUENCE: 6
ctcagcgatg atatagaacg g                                             21

<210> SEQ ID NO 7
<211> LENGTH: 20
<212> TYPE: DNA
<213> ORGANISM: Artificial
<220> FEATURE:
<223> OTHER INFORMATION: probe

<400> SEQUENCE: 7
cagcgatgat atagaacggg                                               20

<210> SEQ ID NO 8
<211> LENGTH: 20
<212> TYPE: DNA
<213> ORGANISM: Artificial
<220> FEATURE:
<223> OTHER INFORMATION: probe

<400> SEQUENCE: 8
ctcaatgatg atatagaacg                                               20

<210> SEQ ID NO 9
<211> LENGTH: 20
<212> TYPE: DNA
<213> ORGANISM: Artificial
<220> FEATURE:
<223> OTHER INFORMATION: probe

<400> SEQUENCE: 9
actcaatgat gatatagaac                                               20

<210> SEQ ID NO 10
<211> LENGTH: 18
<212> TYPE: DNA
<213> ORGANISM: Artificial
<220> FEATURE:

<223> OTHER INFORMATION: probe

<400> SEQUENCE: 10
ttcccgtagg tcatcaac                                           18

<210> SEQ ID NO 11
<211> LENGTH: 17
<212> TYPE: DNA
<213> ORGANISM: Artificial
<220> FEATURE:
<223> OTHER INFORMATION: probe

<400> SEQUENCE: 11
gtcagccacg gagtacc                                            17

<210> SEQ ID NO 12
<211> LENGTH: 21
<212> TYPE: DNA
<213> ORGANISM: Artificial
<220> FEATURE:
<223> OTHER INFORMATION: probe

<400> SEQUENCE: 12
gtttttcttc cccaggtact c                                       21

<210> SEQ ID NO 13
<211> LENGTH: 22
<212> TYPE: DNA
<213> ORGANISM: Artificial
<220> FEATURE:
<223> OTHER INFORMATION: probe

<400> SEQUENCE: 13
gtttttcttc cccaggtact cc                                      22

<210> SEQ ID NO 14
<211> LENGTH: 19
<212> TYPE: DNA
<213> ORGANISM: Artificial
<220> FEATURE:
<223> OTHER INFORMATION: probe

<400> SEQUENCE: 14
gatgacgttt ttcttctcc                                          19

<210> SEQ ID NO 15
<211> LENGTH: 20
<212> TYPE: DNA
<213> ORGANISM: Artificial
<220> FEATURE:
<223> OTHER INFORMATION: probe

<400> SEQUENCE: 15
tgtggatgac gtttttcttc                                         20

<210> SEQ ID NO 16
<211> LENGTH: 24
<212> TYPE: DNA
<213> ORGANISM: Artificial
<220> FEATURE:
<223> OTHER INFORMATION: probe

<400> SEQUENCE: 16
ccagcacggg ctgtgtaggt gtcc                                    24

```
<210> SEQ ID NO 17
<211> LENGTH: 21
<212> TYPE: DNA
<213> ORGANISM: Artificial
<220> FEATURE:
<223> OTHER INFORMATION: sense primer

<400> SEQUENCE: 17
gacaagtggg agatggaacg c                                              21

<210> SEQ ID NO 18
<211> LENGTH: 16
<212> TYPE: DNA
<213> ORGANISM: Artificial
<220> FEATURE:
<223> OTHER INFORMATION: antisense primer

<400> SEQUENCE: 18
cacggccacc gtcagg                                                    16

<210> SEQ ID NO 19
<211> LENGTH: 21
<212> TYPE: DNA
<213> ORGANISM: Artificial
<220> FEATURE:
<223> OTHER INFORMATION: sense primer

<400> SEQUENCE: 19
gacaagtggg agatggaacg c                                              21

<210> SEQ ID NO 20
<211> LENGTH: 16
<212> TYPE: DNA
<213> ORGANISM: Artificial
<220> FEATURE:
<223> OTHER INFORMATION: antisense primer

<400> SEQUENCE: 20
cacggccacc gtcagg                                                    16

<210> SEQ ID NO 21
<211> LENGTH: 33
<212> TYPE: DNA
<213> ORGANISM: Artificial
<220> FEATURE:
<223> OTHER INFORMATION: sense primer

<400> SEQUENCE: 21
ggacggacgg accgtcctcg ttgtcttgtt ggc                                 33

<210> SEQ ID NO 22
<211> LENGTH: 34
<212> TYPE: DNA
<213> ORGANISM: Artificial
<220> FEATURE:
<223> OTHER INFORMATION: antisense primer

<400> SEQUENCE: 22
ggacggacgg accgcactcc ctcaggtagt ccag                                34

<210> SEQ ID NO 23
<211> LENGTH: 33
<212> TYPE: DNA
<213> ORGANISM: Artificial
<220> FEATURE:
<223> OTHER INFORMATION: sense primer
```

<400> SEQUENCE: 23
ggacggacgg accgtcctcg ttgtcttgtt ggc       33

<210> SEQ ID NO 24
<211> LENGTH: 34
<212> TYPE: DNA
<213> ORGANISM: Artificial
<220> FEATURE:
<223> OTHER INFORMATION: antisense primer

<400> SEQUENCE: 24
ggacggacgg accgcactcc ctcaggtagt ccag       34

<210> SEQ ID NO 25
<211> LENGTH: 33
<212> TYPE: DNA
<213> ORGANISM: Artificial
<220> FEATURE:
<223> OTHER INFORMATION: sense primer

<400> SEQUENCE: 25
ggacggacgg accgtcctcg ttgtcttgtt ggc       33

<210> SEQ ID NO 26
<211> LENGTH: 34
<212> TYPE: DNA
<213> ORGANISM: Artificial
<220> FEATURE:
<223> OTHER INFORMATION: antisense primer

<400> SEQUENCE: 26
ggacggacgg accgcactcc ctcaggtagt ccag       34

<210> SEQ ID NO 27
<211> LENGTH: 28
<212> TYPE: DNA
<213> ORGANISM: Artificial
<220> FEATURE:
<223> OTHER INFORMATION: sense primer

<400> SEQUENCE: 27
ggccggcccc gtggtgctgc tgtacatg       28

<210> SEQ ID NO 28
<211> LENGTH: 19
<212> TYPE: DNA
<213> ORGANISM: Artificial
<220> FEATURE:
<223> OTHER INFORMATION: antisense primer

<400> SEQUENCE: 28
cacgccctgt gactccatg       19

<210> SEQ ID NO 29
<211> LENGTH: 28
<212> TYPE: DNA
<213> ORGANISM: Artificial
<220> FEATURE:
<223> OTHER INFORMATION: sense primer

<400> SEQUENCE: 29
ggccggcccc gtggtgctgc tgtacatg       28

<210> SEQ ID NO 30
<211> LENGTH: 19

```
<212> TYPE: DNA
<213> ORGANISM: Artificial
<220> FEATURE:
<223> OTHER INFORMATION: antisense primer

<400> SEQUENCE: 30
cacgccctgt gactccatg                                                      19

<210> SEQ ID NO 31
<211> LENGTH: 28
<212> TYPE: DNA
<213> ORGANISM: Artificial
<220> FEATURE:
<223> OTHER INFORMATION: sense primer

<400> SEQUENCE: 31
ggccggcccc gtggtgctgc tgtacatg                                            28

<210> SEQ ID NO 32
<211> LENGTH: 19
<212> TYPE: DNA
<213> ORGANISM: Artificial
<220> FEATURE:
<223> OTHER INFORMATION: antisense primer

<400> SEQUENCE: 32
cacgccctgt gactccatg                                                      19

<210> SEQ ID NO 33
<211> LENGTH: 33
<212> TYPE: DNA
<213> ORGANISM: Artificial
<220> FEATURE:
<223> OTHER INFORMATION: sense primer

<400> SEQUENCE: 33
acctacctac ctagatcttg ctgcccgaaa ctg                                      33

<210> SEQ ID NO 34
<211> LENGTH: 33
<212> TYPE: DNA
<213> ORGANISM: Artificial
<220> FEATURE:
<223> OTHER INFORMATION: antisense primer

<400> SEQUENCE: 34
acctacctac ctcttgttgt aggccaggct ctc                                      33

<210> SEQ ID NO 35
<211> LENGTH: 16
<212> TYPE: DNA
<213> ORGANISM: Artificial
<220> FEATURE:
<223> OTHER INFORMATION: probe

<400> SEQUENCE: 35
caccgtgaag cacaag                                                         16

<210> SEQ ID NO 36
<211> LENGTH: 14
<212> TYPE: DNA
<213> ORGANISM: Artificial
<220> FEATURE:
<223> OTHER INFORMATION: probe

<400> SEQUENCE: 36
```

-continued ccctcgccca gctt                                                          14

<210> SEQ ID NO 37
<211> LENGTH: 22
<212> TYPE: DNA
<213> ORGANISM: Artificial
<220> FEATURE:
<223> OTHER INFORMATION: probe

<400> SEQUENCE: 37
catgaactca gcgatgatat ag                                                 22

<210> SEQ ID NO 38
<211> LENGTH: 20
<212> TYPE: DNA
<213> ORGANISM: Artificial
<220> FEATURE:
<223> OTHER INFORMATION: probe

<400> SEQUENCE: 38
cccgttctat atcatcgctg                                                    20

<210> SEQ ID NO 39
<211> LENGTH: 22
<212> TYPE: DNA
<213> ORGANISM: Artificial
<220> FEATURE:
<223> OTHER INFORMATION: probe

<400> SEQUENCE: 39
cccgttctat atcatcattg ag                                                 22

<210> SEQ ID NO 40
<211> LENGTH: 19
<212> TYPE: DNA
<213> ORGANISM: Artificial
<220> FEATURE:
<223> OTHER INFORMATION: probe

<400> SEQUENCE: 40
ccgttctata tcatcattg                                                     19

<210> SEQ ID NO 41
<211> LENGTH: 19
<212> TYPE: DNA
<213> ORGANISM: Artificial
<220> FEATURE:
<223> OTHER INFORMATION: probe

<400> SEQUENCE: 41
ttgatgacct acgggaacc                                                     19

<210> SEQ ID NO 42
<211> LENGTH: 18
<212> TYPE: DNA
<213> ORGANISM: Artificial
<220> FEATURE:
<223> OTHER INFORMATION: probe

<400> SEQUENCE: 42
ttgatgacct acgggaac                                                      18

<210> SEQ ID NO 43
<211> LENGTH: 18
<212> TYPE: DNA
<213> ORGANISM: Artificial

```
<220> FEATURE:
<223> OTHER INFORMATION: probe

<400> SEQUENCE: 43
cccgtaggtc atcaactc                                                   18

<210> SEQ ID NO 44
<211> LENGTH: 30
<212> TYPE: DNA
<213> ORGANISM: Artificial
<220> FEATURE:
<223> OTHER INFORMATION: probe

<400> SEQUENCE: 44
ccactcagat ctcgtcagcc acggagtacc                                      30

<210> SEQ ID NO 45
<211> LENGTH: 20
<212> TYPE: DNA
<213> ORGANISM: Artificial
<220> FEATURE:
<223> OTHER INFORMATION: probe

<400> SEQUENCE: 45
ccatggagta cctagcgaag                                                 20

<210> SEQ ID NO 46
<211> LENGTH: 16
<212> TYPE: DNA
<213> ORGANISM: Artificial
<220> FEATURE:
<223> OTHER INFORMATION: probe

<400> SEQUENCE: 46
cttccccagg tactcc                                                     16

<210> SEQ ID NO 47
<211> LENGTH: 18
<212> TYPE: DNA
<213> ORGANISM: Artificial
<220> FEATURE:
<223> OTHER INFORMATION: probe

<400> SEQUENCE: 47
ctgtggatga cgttttc                                                    18

<210> SEQ ID NO 48
<211> LENGTH: 19
<212> TYPE: DNA
<213> ORGANISM: Artificial
<220> FEATURE:
<223> OTHER INFORMATION: probe

<400> SEQUENCE: 48
cctgtggatg acgttttc                                                   19

<210> SEQ ID NO 49
<211> LENGTH: 27
<212> TYPE: DNA
<213> ORGANISM: Artificial
<220> FEATURE:
<223> OTHER INFORMATION: probe

<400> SEQUENCE: 49
gctccagcac gggctgtgta ggtgtcc                                         27
```

```
<210> SEQ ID NO 50
<211> LENGTH: 18
<212> TYPE: DNA
<213> ORGANISM: Artificial
<220> FEATURE:
<223> OTHER INFORMATION: probe

<400> SEQUENCE: 50
ccagcacggg ctgtgtag                                                        18
```

PROBE FOR DETECTING ABL GENE MUTATION AND USES THEREOF

TECHNICAL FIELD

The present invention relates to probes for detecting mutations in abl genes relevant to leukemia and the uses thereof.

BACKGROUND ART

Detection of point mutation, so-called single nucleotide polymorphism (SNP), is employed widely as a method of analyzing, at the gene level, for example, the causes of all types of diseases and the individual differences in disease liability (susceptibility to diseases) and in drug action.

Examples of the common methods of detecting a point mutation include: (1) a direct sequencing method in which the region corresponding to a sequence to be detected in the target DNA of a sample is amplified and all the gene sequences are analyzed, (2) a pyrosequencing method, (3) a denaturing HPLC method in which the region corresponding to a sequence to be detected is amplified, HPLC is performed in a temperature gradient column, and the presence or absence of any mutation is detected according to the time that is required for elution, (4) an invader method in which, using fluorescence that is emitted when a fluorescent probe binds to the region containing a target mutation, a mutation is detected through detection of the fluorescence, and (5) the ASP-PCR method in which PCR is performed using a primer with a target mutation located at the 3'-end region and the mutation is judged depending on the presence or absence of amplification.

However, the aforementioned methods (1), (2), and (4) are not very sensitive, specifically their sensitivity is approximately 20%, approximately 5%, and approximately 5%, respectively, and they require a considerable amount of time and labor for their operations. Furthermore, in the aforementioned method (3), the sensitivity is as low as approximately 10%, it only can check the presence or absence of a mutation, and it cannot analyze the site and type of a mutation. Therefore, there is a problem in that it lacks specificity. The aforementioned method (5) is highly sensitive but is less specific, so that it is apt to give a false-positive result, which is a problem. In this context, the lower the numerical value (%) is, the relatively higher the sensitivity.

Because of these problems, recently, a method of analyzing the melting temperature (Tm) of double-stranded nucleic acid formed of a probe and target nucleic acid is used as a method of detecting a point mutation. Since this method is performed through, for example, Tm analysis or analysis of the melting curve of the double strand, it is referred to as melting curve analysis. This is a method as described below. That is, first, a probe complementary to a sequence to be detected containing a target point mutation is used to form a hybrid (double-stranded DNA) between the aforementioned probe and a target single-stranded DNA in a detection sample. Subsequently, this hybridization product is heat-treated, so that dissociation (melting) of the hybrid accompanying the temperature rise is detected by a change in the signal such as absorbance. The Tm value is then determined based on the result of the detection and the presence or absence of any point mutation is judged accordingly. The higher the Tm value, the higher the homology of the hybridization product, and the lower the Tm value, the lower the homology. Therefore the Tm value (reference value for assessment) is determined beforehand for the hybridization product between the sequence to be detected containing a point mutation and a probe complementary thereto and then the Tm value (measured value) of the hybridization product between the target single-stranded DNA in the detection sample and the aforementioned probe is measured. When the measured value is equal to the reference value, it is considered as matching, that is, it can be judged that the point mutation is present in the target DNA. On the other hand, when the measured value is lower than the reference value, it is considered as mismatching, that is, it can be judged that no point mutation is present in the target DNA.

However, such a detection method using Tm analysis also has a problem in that the sensitivity is low. This is a problem, particularly, in detecting point mutations in DNAs derived from blood cells of leukemia patients (Patent Document 1). Leukemia is a disease resulting from malignant transformation of hematopoietic stem cells in the bone marrow. Chronic myeloid leukemia (CML), among others, is known to have its origin in the bcr-abl fusion gene generated by translocation between chromosome 9 and chromosome 22 and, for example, imatinib, an ABL kinase inhibitor, is used widely for the treatment of the disease. However, when a point mutation is present in the abl gene (including the abl gene in the aforementioned fusion gene), resistance to imatinib is developed, which is a problem. In that case, an increase in dose of imatinib, a change to some other therapeutic drug, or switching to, for example, bone marrow transplantation becomes necessary for the treatment. Therefore in the treatment of leukemia, particularly CML, it is very important to detect the presence or absence of a point mutation in the abl gene. However, even in the blood of the same CML patient, there are blood cells with point mutations that have occurred in the abl genes (mutated genes) and those with no point mutations that have occurred in the abl genes (normal genes), and the difference between them resides merely in a point mutation, that is, a single base of the sequence. Then a phenomenon may occur where the probe for detecting a point mutation hybridizes (perfectly matches) with the mutated sequence (the sequence to be detected) containing the point mutation and also hybridizes (mismatches) with a normal sequence (sequence not to be detected) that does not contain the point mutation. In such a case, when a melting curve that indicates the relationship between signal intensity and temperature is prepared based on Tm analysis, it is difficult to detect the peak on the higher temperature side that corresponds to the perfectly matched mutated sequence due to the presence of the peak on the lower temperature side that corresponds to the mismatched normal sequence, which is a problem. That is, even when a mutated sequence containing a mutation is present, the presence of a normal sequence containing no mutation makes it difficult for the conventional probe to detect the presence of the mutated sequence, which causes a decrease in detection sensitivity.

[Patent Document 1] JP 2004-537992 A

DISCLOSURE OF INVENTION

Hence, the present invention is intended to provide a detection probe capable of detecting a sequence to be detected containing a mutation even when a sequence not to be detected containing no mutation coexists with the sequence to be detected containing a mutation, which are different only in a single base from each other, and to provide the uses thereof.

In order to achieve the aforementioned object, the probe of the present invention is a probe for detecting a mutation in an abl gene and is characterized by being composed of at least one oligonucleotide selected from the group consisting of the following (A1) to (I1):

(A1) oligonucleotide consisting of the base sequence of SEQ ID NO: 2,
(A2) oligonucleotide consisting of the base sequence of SEQ ID NO: 3,
(B1) oligonucleotide consisting of the base sequence of SEQ ID NO: 4,
(B2) oligonucleotide consisting of the base sequence of SEQ ID NO: 5,
(C1) oligonucleotide consisting of the base sequence of SEQ ID NO: 6,
(C2) oligonucleotide consisting of the base sequence of SEQ ID NO: 7,
(D1) oligonucleotide consisting of the base sequence of SEQ ID NO: 8,
(D2) oligonucleotide consisting of the base sequence of SEQ ID NO: 9,
(E1) oligonucleotide consisting of the base sequence of SEQ ID NO: 10,
(F1) oligonucleotide consisting of the base sequence of SEQ ID NO: 11,
(G1) oligonucleotide consisting of the base sequence of SEQ ID NO: 12,
(G2) oligonucleotide consisting of the base sequence of SEQ ID NO: 13,
(H1) oligonucleotide consisting of the base sequence of SEQ ID NO: 14,
(H2) oligonucleotide consisting of the base sequence of SEQ ID NO: 15, and
(I1) oligonucleotide consisting of the base sequence of SEQ ID NO: 16.

A method of detecting a mutation of the present invention is a method of detecting a mutation in an abl gene and is characterized by including the following steps (1) to (3):
(1) preparing a reaction solution including a sample containing DNA and a probe of the present invention,
(2) measuring signal values that indicate the melting states of a hybridization product between the DNA and the probe while changing the temperature of the reaction solution, and
(3) determining the presence or absence of the mutation from a change in the signal values accompanying a change in the temperature.

Even when an abl gene in which a target mutation to be detected has occurred (mutated gene) coexists with an abl gene in which no mutation has occurred (normal gene), the probe of the present invention makes it possible to detect the sequence to be detected in which the target mutation has occurred. For example, in the Tm analysis, since a conventional probe hybridizes with both a normal gene and a mutated gene, which are different only in a single base from each other, signal behaviors (for example, signal peaks) of both overlap each other in the melting curve, which results in considerable difficulty in detecting the presence of the mutated gene. On the other hand, according to the probe of the present invention, even if the probe hybridizes with both a mutated gene and a normal gene, the signal peaks of both can be separated sufficiently in the melting curve. Therefore the present invention allows a mutated gene to be detected with higher sensitivity as compared to a conventional probe. In the present invention, the term "abl gene" embraces an abl gene in a bcr-abl fusion gene (the same applies below).

BEST MODE FOR CARRYING OUT THE INVENTION

Figure 1:
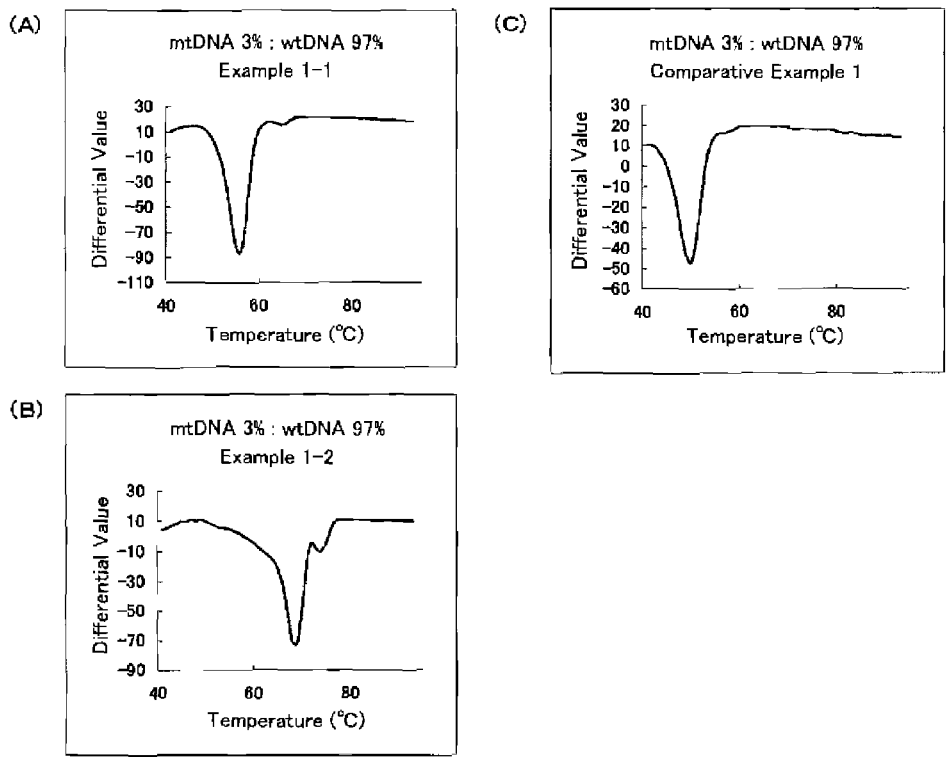
FIG. 1 shows graphs indicating the results of Tm analysis in an example of the present invention.

In the present invention, an abl gene in which a target mutation to be detected has occurred may be referred to as a "mutated gene or gene to be detected", a sequence, in which a target mutation to be detected has occurred, to be detected by a probe may be referred to as a "mutated sequence or sequence to be detected", an abl gene in which no target mutation to be detected has occurred may be referred to as a "normal gene or gene not to be detected", a sequence in which no target mutation to be detected has occurred may be referred to as a "normal sequence or sequence not to be detected", and the DNA contained in a sample for detecting the presence or absence of a mutation may be referred to as a "target DNA". The mutation to be detected in the present invention is, for example, single nucleotide polymorphism (SNP).

<Probe>

The probe of the present invention is a probe for detecting a mutation in an abl gene and is characterized by being composed of at least one oligonucleotide selected from the group consisting of the aforementioned (A1) to (I1). The cDNA sequence (mRNA sequence) of the abl gene is shown in SEQ ID NO: 1. This sequence has been registered at NCBI under the accession No. NM_005157. Those probes are described below.

The probes composed of the following oligonucleotides (A1) and (A2) are each a probe for detecting a mutation (A→G) of A at base 730 in the base sequence of SEQ ID NO: 1. The following oligonucleotide of SEQ ID NO: 2 or SEQ ID NO: 3 allows a mutation in a forward strand to be checked, while the oligonucleotide complementary thereto allows a mutation in a reverse strand to be checked.
(A1) oligonucleotide consisting of the base sequence of SEQ ID NO: 2 or oligonucleotide complementary thereto
(A2) oligonucleotide consisting of the base sequence of SEQ ID NO: 3 or oligonucleotide complementary thereto

```
                                           (SEQ ID NO: 2)
       5'-tgtgcttcaCggtgatgtcc-3'

(SEQ ID NO: 3)
       5'-gtgcttcaCggtgatgtccgtgcgttcc-3'
```

The probes composed of the following oligonucleotides (B1) and (B2) are each a probe for detecting a mutation (G→A) of G at base 749 in the base sequence of SEQ ID NO: 1. The following oligonucleotide of SEQ ID NO: 4 or SEQ ID NO: 5 allows a mutation in a reverse strand to be checked, while the oligonucleotide complementary thereto allows a mutation in a forward strand to be checked.
(B1) oligonucleotide consisting of the base sequence of SEQ ID NO: 4 or oligonucleotide complementary thereto
(B2) oligonucleotide consisting of the base sequence of SEQ ID NO: 5 or oligonucleotide complementary thereto (SEQ ID NO: 4)
5'-caagctgggcgAgggcc-3'

(SEQ ID NO: 5)
5'-cacaagctgggcgAggg-3'

The probes composed of the following oligonucleotides (C1) and (C2) are each a probe for detecting a mutation (A→G) of A at base 943 in the base sequence of SEQ ID NO: 1. The following oligonucleotide of SEQ ID NO: 6 or SEQ ID NO: 7 allows a mutation in a forward strand to be checked, while the oligonucleotide complementary thereto allows a mutation in a reverse strand to be checked.
(C1) oligonucleotide consisting of the base sequence of SEQ ID NO: 6 or oligonucleotide complementary thereto
(C2) oligonucleotide consisting of the base sequence of SEQ ID NO: 7 or oligonucleotide complementary thereto (SEQ ID NO: 6)
5'-ctcagCgatgatatagaacgg-3'

(SEQ ID NO: 7)
5'-cagCgatgatatagaacggg-3'

The probes composed of the following oligonucleotides (D1) and (D2) are each a probe for detecting a mutation (C→T) of C at base 944 in the base sequence of SEQ ID NO: 1. The following oligonucleotide of SEQ ID NO: 8 or SEQ ID NO: 9 allows a mutation in a forward strand to be checked, while the oligonucleotide complementary thereto allows a mutation in a reverse strand to be checked.
(D1) oligonucleotide consisting of the base sequence of SEQ ID NO: 8 or oligonucleotide complementary thereto
(D2) oligonucleotide consisting of the base sequence of SEQ ID NO: 9 or oligonucleotide complementary thereto (SEQ ID NO: 8)
5'-ctcaAtgatgatatagaacg-3'

(SEQ ID NO: 9)
5'-actcaAtgatgatatagaac-3'

Each probe composed of the following oligonucleotide (E1) is a probe for detecting a mutation (C→G) of C at base 951 in the base sequence of SEQ ID NO: 1. The following oligonucleotide of SEQ ID NO: 10 allows a mutation in a forward strand to be checked, while the oligonucleotide complementary thereto allows a mutation in a reverse strand to be checked.
(E1) oligonucleotide consisting of the base sequence of SEQ ID NO: 10 or oligonucleotide complementary thereto (SEQ ID NO: 10)
5'-ttcccgtaggtcatCaac-3'

Each probe composed of the following oligonucleotide (F1) is a probe for detecting a mutation (T→C) of T at base 1052 in the base sequence of SEQ ID NO: 1. The following oligonucleotide of SEQ ID NO: 11 allows a mutation in a reverse strand to be checked, while the oligonucleotide complementary thereto allows a mutation in a forward strand to be checked.
(F1) oligonucleotide consisting of the base sequence of SEQ ID NO:11 or oligonucleotide complementary thereto (SEQ ID NO: 11)
5'-gtcagccaCggagtacc-3'

The probes composed of the following oligonucleotides (G1) and (G2) are each a probe for detecting a mutation (A→G) of A at base 1064 in the base sequence of SEQ ID NO: 1. The following oligonucleotide of SEQ ID NO: 12 or SEQ ID NO: 13 allows a mutation in a forward strand to be checked, while the oligonucleotide complementary thereto allows a mutation in a reverse strand to be checked.
(G1) oligonucleotide consisting of the base sequence of SEQ ID NO: 12 or oligonucleotide complementary thereto
(G2) oligonucleotide consisting of the base sequence of SEQ ID NO: 13 or oligonucleotide complementary thereto (SEQ ID NO: 12)
5'-gtttttcttcCccaggtactc-3'

(SEQ ID NO: 13)
5'-gtttttcttcCccaggtactcc-3'

The probes composed of the following oligonucleotides (H1) and (H2) are each a probe for detecting a mutation (T→G) of T at base 1075 in the base sequence of SEQ ID NO: 1. The following oligonucleotide of SEQ ID NO: 14 or SEQ ID NO: 15 allows a mutation in a forward strand to be checked, while the oligonucleotide complementary thereto allows a mutation in a reverse strand to be checked.
(H1) oligonucleotide consisting of the base sequence of SEQ ID NO: 14 or oligonucleotide complementary thereto
(H2) oligonucleotide consisting of the base sequence of SEQ ID NO: 15 or oligonucleotide complementary thereto (SEQ ID NO: 14)
5'-gatgaCgtttttcttctcc-3'

(SEQ ID NO: 15)
5'-tgtggatgaCgtttttcttc-3'

The probe composed of the following oligonucleotide (I1) is a probe for detecting a mutation (A→G) of A at base 1187 in the base sequence of SEQ ID NO: 1. The following oligonucleotide of SEQ ID NO: 16 allows a mutation in a forward strand to be checked, while the oligonucleotide complementary thereto allows a mutation in a reverse strand to be checked.
(I1) oligonucleotide consisting of the base sequence of SEQ ID NO: 16 or oligonucleotide complementary thereto (SEQ ID NO: 16)
5'-ccagcaCgggctgtgtaggtgtcc-3'

Preferably, the probe of the present invention is labeled. The probe is labeled with, for example, a fluorescent dye (fluorophore). A specific example of the labeled probe is preferably a probe that has been labeled with the fluorescent dye, exhibits fluorescence independently, and allows fluorescence to be reduced (for example, quenched) after hybridization. A probe that utilizes such a fluorescence quenching phenomenon is referred to as a fluorescence quenching probe. Particularly, with respect to the aforementioned probe, it is preferable that the 3' end or 5' end of oligonucleotide be labeled with a fluorescent dye and the base at the end to be labeled be C. In this case, in the sequence to be detected, to which the labeled probe hybridizes, it is preferable that the base sequence of the labeled probe be designed so that the base to be paired with the end base C of the labeled probe or the base located 1 to 3 bases apart from the base to be paired be G. Generally, such a probe is referred to as a guanine quenching probe and is known as so-called QProbe (registered trademark). When such a guanine quenching probe hybridizes to a sequence to be detected, C at the end, which has been labeled with a fluorescent dye, approaches G in the DNA to be detected, and thereby a phenomenon occurs that the emission of the fluorescent dye decreases (the fluorescence intensity decreases). The use of such a probe makes it possible to verify hybridization and dissociation easily according to a change in the signal.

Examples thereof Examples of the fluorescent dye include fluorescein, phosphor, rhodamine, and polymethine dye derivative. Examples of commercially available fluorescent dye include BODIPY FL (trademark, manufactured by Molecular Probe Inc.), FluorePrime (trade name, manufactured by Amersham Pharmacia), Fluoredite (trade name, manufactured by Millipore Corporation), FAM (manufactured by ABI), Cy3 and Cy5 (manufactured by Amersham Pharmacia), and TAMRA (manufactured by Molecular Probe Inc.). Conditions for detecting probes are not particularly limited and can be determined suitably according to the fluorescent dye to be used. For example, Pacific Blue can be detected with a detection wavelength of 450 to 480 nm, TAMRA with a detection wavelength of 585 to 700 nm, and BODIPY FL with a detection wavelength of 515 to 555 nm. The use of such a probe makes it possible to verify hybridization and dissociation easily according to a change in the signal. Furthermore, when two types of mutations are to be detected in the same reaction solution, at least two types of probes corresponding to the respective mutations can be used in combination. In this case, labeling the respective probes with fluorescent dyes that can be detected with different detection wavelengths from each other also allows two types or more of mutations to be detected using the same reaction solution.

A probe of the present invention may include, for example, a phosphate group added to the 3' end. As described later, DNA (target DNA) in which the presence or absence of a mutation is to be detected can be prepared by a gene amplification method such as PCR, during which the probe of the present invention is allowed to coexist in the reaction solution for the gene amplification reaction. In such a case, addition of a phosphate group to the 3' end of the probe can satisfactorily prevent the probe itself from being elongated by the gene amplification reaction. Furthermore, addition of a labeling substance as described above to the 3' end also provides the similar effect.

As described above, the probe of the present invention can be used for detecting a mutation in an abl gene. The detection method is not limited at all as long as it is a method that utilizes hybridization between the probe and a sequence to be detected. A method of detecting a mutation using Tm analysis is described below as an example of the method in which a probe of the present invention is used.

<Mutation Detection Method>

The mutation detection method of the present invention is a method of detecting a mutation in an abl gene as described above and is characterized by including the following steps (1) to (3). The mutation detection method of the present invention is characterized by using a probe of the present invention and, for example, the other configuration and conditions are not limited to the following description.

(1) preparing a reaction solution including a sample containing DNA and a probe of the present invention
(2) measuring the signal values that indicate melting states of a hybridization product between the DNA and the probe while changing the temperature of the reaction solution
(3) determining the presence or absence of the mutation from a change in the signal values accompanying a change in the temperature.

In the present invention, the DNA contained in the sample may be single-stranded DNA or double-stranded DNA. When the DNA is double-stranded DNA, it is preferable that, for example, a step of dissociating the double-stranded DNA by heating be included before the aforementioned step (2). Dissociation of the double-stranded DNA into single-stranded DNA allows it to hybridize to a probe of the present invention.

In the present invention, DNA contained in a sample may be, for example, DNA contained originally in a biological sample. However, it is preferably an amplification product obtained through amplification carried out by, for example, PCR using nucleic acid contained originally in a biological sample as a template, because the detection accuracy can be improved. The length of the amplification product is not particularly limited and is, for example, 50- to 1000-mers, preferably 80- to 200-mers. The nucleic acid may be, for example, DNA or RNA (for instance, total RNA or mRNA), or may be, for example, cDNA synthesized from the RNA by reverse transcription PCR (RT-PCR).

The sample, with respect to which the mutation detection method of the present invention is used, is not particularly limited. An example thereof is a sample with an abl gene present therein. Specific examples thereof include a whole blood sample as well as blood cell samples such as a white blood cell. In the present invention, for example, the sampling method and DNA preparation method are not limited, and conventionally known methods can be employed.

In the present invention, the ratio (molar ratio) of the probe of the present invention to be added to DNA contained in the sample is not limited. For example, from the view point of obtaining detection signals sufficiently, the ratio is preferably 1:1 or lower and more preferably 0.1:1 or lower. In this case, the DNA contained in the sample may be, for example, the total of DNA to be detected in which a target mutation to be detected has occurred and DNA not to be detected in which the mutation has not occurred, or the total of an amplification product containing a sequence to be detected in which a target mutation to be detected has occurred and an amplification product containing a sequence not to be detected in which the mutation has not occurred Generally, the ratio of the DNA to be detected in the DNA contained in a sample is unknown. However, in terms of results, the ratio (molar ratio) of the probe to be added to the DNA to be detected (an amplification product containing a sequence to be detected) is preferably 10:1 or lower, more preferably 5:1 or lower, and further preferably 3:1 or lower. Moreover, the lower limit thereof is not particularly limited and is, for example, at least 0.001:1, preferably at least 0.01:1, and more preferably at least 0.1:1.

The ratio of the probe of the present invention to be added to the DNA may be, for example, the molar ratio thereof to double-stranded DNA or the molar ratio thereof to single-stranded DNA.

The Tm value is described below. When a solution containing double-stranded DNA is heated, the absorbance at 260 nm increases. This is because heating releases the hydrogen bond between both strands in the double-stranded DNA to dissociate it into single-stranded DNA (melting of DNA). When all double-stranded DNAs are dissociated into single-stranded DNAs, the absorbance thereof indicates approximately 1.5 times that is obtained at the start of heating (i.e. absorbance of only double-stranded DNAs), which makes it possible to judge that melting is completed thereby. Based on this phenomenon, the melting temperature Tm generally is defined as a temperature at which the absorbance has reached 50% of the total increase in absorbance.

In the aforementioned step (2) of the present invention, the measurement of the signal values that indicate the melting states of a hybridization product between the DNA and the probe may be a measurement of absorbance at 260 nm based on the principle as described above but is preferably measurement of the signal of a labeling substance added to the probe of the present invention. Accordingly, it is preferable that the aforementioned labeled probe be used as the probe of the present invention. The labeled probe can be, for example, a labeled probe that exhibits a signal independently but does not exhibit a signal after hybridization, or a labeled probe that does not exhibit a signal independently but exhibits a signal after hybridization. The former probe does not exhibit a signal after forming a hybrid (double-stranded DNA) with a sequence to be detected but exhibits a signal when the probe is released by heating. On the other hand, the latter probe exhibits a signal after forming a hybrid (double-stranded DNA) with a sequence to be detected but the signal is reduced (quenched) when the probe is released by heating. Accordingly, when the signal exhibited by the labeling substance is detected under a condition (for example, absorbance) specific to the signal, the progress of melting and the Tm value can be determined as in the case of the measurement of absorbance at 260 nm. The labeling substance of the labeled probe is, for example, as described above.

Next, the mutation detection method of the present invention is described using an example in which a probe labeled with a fluorescent dye is used as a probe of the present invention. The mutation detection method of the present invention is characterized by the use of a probe of the present invention itself and is not limited by other steps or conditions by any means.

First, genomic DNA is isolated from whole blood. Isolation of genomic DNA from whole blood can be carried out by a conventionally known method. For example, a commercially available genomic DNA isolation kit (trade name: GFX Genomic Blood DNA Purification kit; manufactured by GE Healthcare Bioscience) can be used.

Next, a labeled probe of the present invention is added to a sample containing the genomic DNA thus isolated. Preferably, the labeled probe is, for example, QProbe as described above. The QProbe generally is a probe in which a cytosine base at the end thereof is labeled with a fluorescent dye. When it hybridizes to a sequence to be detected, the fluorescent dye and a guanine base of the sequence to be detected interact with each other and as a result, the fluorescence decreases (or quenches). The sequence of the labeled probe is as described above, and may be selected suitably according to the target mutation to be detected.

The timing for adding the detection probe is not particularly limited. For instance, it may be added to the amplification product after the gene amplification process to be described later or before the gene amplification process. When the detection probe is added before the amplification process that is carried out by, for example, PCR as described above, it is preferable that, for example, as described above, a fluorescent dye be added to the 3' end thereof or a phosphate group be added thereto.

The aforementioned detection probe may be added to a liquid sample containing isolated genomic DNA or may be mixed with genomic DNA in a solvent. The solvent is not particularly limited. Examples thereof include conventionally known solvents such as buffer solutions such as Tris-HCl, solvents containing, for example, KCl, $MgCl_2$, $MgSO_4$, or glycerol, and gene amplification reaction solutions.

Subsequently, with isolated genomic DNA used as a template, a sequence containing a site where a point mutation to be detected occurs (sequence to be detected and sequence not to be detected) is amplified by a gene amplification method such as PCR. The gene amplification method is not limited. Examples thereof include the polymerase chain reaction (PCR) method, a nucleic acid sequence based amplification (NASBA) method, a transcription-mediated amplification (TMA) method, and a strand displacement amplification (SDA) method. Particularly, the PCR method is preferable. The present invention is described below using the PCR method as an example but is not limited thereby. The PCR conditions are not particularly limited and it can be carried out by the conventionally known method.

The sequence of a primer for PCR is not particularly limited as long as it can amplify a target sequence to be detected. It can be designed suitably by a conventionally known method according to the target sequence. The length of the primer is not particularly limited and can be set at a general length, for example, 10- to 30-mers. Examples of the primer set that can be used for amplifying a sequence to be detected when the aforementioned probes (A1) to (I1) are used are indicated below. These are examples and do not limit the present invention.

```
Primer set for A1 probe and A2 probe
Sense primer
                                      SEQ ID NO: 17
5'-gacaagtgggagatggaacgc-3'

Antisense primer
                                      SEQ ID NO: 18
5'-cacggccaccgtcagg-3'

Primer set for B1 probe and B2 probe
Sense primer
                                      SEQ ID NO: 19
5'-gacaagtgggagatggaacgc-3'

Antisense primer
                                      SEQ ID NO: 20
5'-cacggccaccgtcagg-3'

Primer set for C1 probe and C2 probe
Sense primer
                                      SEQ ID NO: 21
5'-ggacggacggaccgtcctcgttgtcttgttggc-3'

Antisense primer
                                      SEQ ID NO: 22
5'-ggacggacggaccgcactccctcaggtagtccag-3'

Primer set for D1 probe and D2 probe
Sense primer
                                      SEQ ID NO: 23
5'-ggacggacggaccgtcctcgttgtcttgttggc-3'

Antisense primer
                                      SEQ ID NO: 24
5'-ggacggacggaccgcactccctcaggtagtccag-3'
```

-continued

```
Primer set for E1 probe
Sense primer
                                    SEQ ID NO: 25
5'-ggacggacggaccgtcctcgttgtcttgttggc-3'

Antisense primer
                                    SEQ ID NO: 26
5'-ggacggacggaccgcactccctcaggtagtccag-3'

Primer set for F1 probe
Sense primer
                                    SEQ ID NO: 27
5'-ggccggccccgtggtgctgctgtacatg-3'

Antisense primer
                                    SEQ ID NO: 28
5'-cacgccctgtgactccatg-3'

Primer set for G1 probe and G2 probe
Sense primer
                                    SEQ ID NO: 29
5'-ggccggccccgtggtgctgctgtacatg-3'

Antisense primer
                                    SEQ ID NO: 30
5'-cacgccctgtgactccatg-3'

Primer set for H1 probe and H2 probe
Sense primer
                                    SEQ ID NO: 31
5'-ggccggccccgtggtgctgctgtacatg-3'

Antisense primer
                                    SEQ ID NO: 32
5'-cacgccctgtgactccatg-3'

Primer set for I1 probe
Sense primer
                                    SEQ ID NO: 33
5'-acctacctacctagatcttgctgcccgaaactg-3'

Antisense primer
                                    SEQ ID NO: 34
5'-acctacctacctcttgttgtaggccaggctctc-3'
```

Next, the resultant PCR amplification product is dissociated and the single-stranded DNA obtained thereby is hybridized with the labeled probe. This can be carried out by, for example, changing the temperature of the reaction solution.

The heating temperature employed in the dissociation step is not particularly limited as long as it allows the amplification product to be dissociated. It is, for example, 85 to 95° C. The heating time also is not particularly limited and generally is 1 second to 10 minutes, preferably 1 second to 5 minutes.

The dissociated single-stranded DNA can be hybridized with the labeled probe by, for example, decreasing the heating temperature in the dissociation step after the dissociation step. The temperature condition is, for example, 40 to 50° C.

The volume or concentration of each composition in the reaction solution is not particularly limited. Specifically, the concentration of DNA in the reaction solution is, for example, 0.01 to 1 µM, preferably 0.1 to 0.5 µM, and the concentration of the labeled probe is preferably in a range that satisfies, for example, the ratio thereof to be added to the DNA, for instance, 0.001 to 10 µM, preferably 0.001 to 1 µM.

The temperature of the reaction solution further is changed and thereby signal values that indicate the melting states of a hybridization product between the amplification product and the labeled probe are measured. Specifically, for example, the reaction solution containing the hybridization product between the single-stranded DNA and the labeled probe is heated, and thereby the change in the signal values accompanying the temperature rise is measured. As described above, when, for example, a probe (guanine quenching probe), in which the base C at the end has been labeled, is used, fluorescence decreases (or quenches) in the state where the probe has been hybridized with the single-stranded DNA, while fluorescence is emitted in the state where the probe has been dissociated. Accordingly, for example, the hybridization product in which the fluorescence has decreased (or quenched) is heated gradually and thereby the increase in fluorescence intensity accompanying the temperature rise may be measured.

The temperature range in which the change in fluorescence intensity is measured is not particularly limited. For example, the start temperature is room temperature to 85° C., preferably 25 to 70° C., while the end temperature is, for example, 40 to 105° C. Furthermore, the rate of temperature climb is not particularly limited and is, for example, 0.1 to 20° C./sec, preferably 0.3 to 5° C./sec.

In the present invention, it also is possible to detect, for example, two or more different mutations using the same reaction solution. In this case, it is preferable that as described above, labeled probes with different labeling substances added thereto be used as the probes corresponding to the respective mutations. In this measurement step, it is preferable that the signal fluorescence intensity of each labeling substance be measured at a detection wavelength corresponding to each labeling substance.

Next, the Tm value is determined by analyzing a change in the signal. Specifically, the amount of change in the fluorescence intensity per unit time (-d fluorescence intensity increase /dt) at each temperature is calculated from the fluorescence intensity obtained and the temperature at which the lowest value is obtained is determined as the Tm value. It also is possible that the point at which the amount of change in the fluorescence intensity per unit time (d fluorescence intensity increase/dt) is the highest is determined as the Tm value. On the contrary, the amount of decrease in the fluorescence intensity is measured when the labeled probe used is not a quenching probe but a probe that does not exhibit a signal independently but exhibits a signal after hybridization.

From such a Tm value, the genotype in the sequence to be detected is determined. In the Tm analysis, the case of a perfectly complementary hybrid (perfect match) results in a higher Tm value indicating dissociation than that obtained in the case of a hybrid including a different single base (mismatch). Accordingly, when with respect to the probe, the Tm value obtained in the case of a perfectly complementary hybrid and the Tm value obtained in the case of a hybrid including a different single base are determined beforehand, the genotype at each site to be detected can be determined. For example, in the case where the base at the site to be detected is assumed to be of a mutation type (for instance, G at the base 730 in SEQ ID NO: 1), when using a probe (SEQ ID NO: 2 or 3) complementary to the sequence to be detected containing the base, the polymorphism of the amplification product can be judged as a mutation type if the Tm value of the resultant hybrid is equal to the Tm value of a perfectly complementary hybrid. Furthermore, the polymorphism of the amplification product can be judged as a wildtype (for example, A at the base 730 in SEQ ID NO: 1) if the Tm value of the resultant hybrid is equal to the Tm value of the mismatch hybrid including a different single base (i.e. a lower value than the Tm value of the perfectly complementary hybrid). Furthermore, the amplification product can be judged to be mutated homozygous when only the Tm value of the perfectly complementary hybrid was detected, while it can be judged to be wildtype homozygous when only the Tm value of the mismatching hybrid was detected. On the other hand, it can be determined to be heterozygous when both the Tm values were detected.

Thus, the genotype can be judged from the two Tm values with respect to the respective labeled probes.

In the present invention, it is preferable that the Tm value of a perfect match hybridization product and the Tm value of mismatch hybridization product be determined beforehand with respect to each probe. Comparison between the Tm values to serve as evaluation criteria thus determined beforehand and the Tm values obtained when a hybrid is formed actually with a sequence to be detected makes it possible to easily determine the presence or absence of a mutation and the type of zygote. The Tm values to serve as the evaluation criteria can be determined by using, for example, the conventionally known MELTCALC software or the nearest neighbor method. It also is possible to determine them by actually forming a hybrid between a probe of the present invention and a sequence to be detected and performing the Tm analysis.

In the present invention, for example, a change in the signal during hybridization may be measured instead of the method in which the temperature of a reaction solution containing a hybridization product is increased (heating) and a change in the signal accompanying the temperature rise is measured as described above. In other words, when the temperature of the reaction solution containing the aforementioned probe is decreased to form a hybridization product, the change in the signal accompanying the temperature decrease may be measured.

Specifically, when using a labeled probe that exhibits a signal independently but does not exhibit a signal after hybridization (for example, a guanine quenching probe), the labeled probe emits fluorescence in the state where single-stranded DNA and the probe are dissociated, but the fluorescence decreases (or quenches) when a hybrid is formed through temperature decrease. Accordingly, for example, the temperature of the reaction solution is decreased gradually and thereby the decrease in fluorescence intensity accompanying the temperature decrease may be measured. On the other hand, when using a labeled probe that does not exhibits a signal independently but exhibits a signal after hybridization, the labeled probe does not emit fluorescence in the state where single-stranded DNA and the probe are dissociated, but the fluorescence is emitted when a hybrid is formed through temperature decrease. Accordingly, for example, the temperature of the reaction solution is decreased gradually and thereby the increase in fluorescence intensity accompanying the temperature decrease may be measured.

<Probe Kit>

A probe kit of the present invention is a probe kit to be used for detecting a mutation in an abl gene and is characterized by including a probe of the present invention. The probe kit of the present invention may include one type of probe of the present invention or at least two types thereof. In the latter case, at least two types of probes may be contained in a mixed state or may be contained as separate reagents. Furthermore, when at least two types of probes of the present invention are contained in the mixed state in the probe kit of the present invention or when they are contained as separate reagents but, for example, Tm analysis of each probe and each sequence to be detected is carried out in the same reaction system at the time of use, it is preferable that the respective probes be labeled with different labeling substances from each other. In this manner, different types of labeling substances allow detection to be performed with respect to each probe even in the same reaction system. Preferably, the labeling substances are, for example, substances that are different in detection wavelength from each other.

As described above, in an abl gene, a plurality of mutations relative to leukemia have been known. The probes of the present invention allow various mutations (nine types) described above to be detected. On the other hand, in the abl gene involved in leukemia, although, for example, only one mutation may be detected, a plurality of mutations may be detected. A plurality of mutations to be detected in the present invention are mutations that indicate the relationship with leukemia or a drug for it (for example, imatinib). Conceivably, each mutation indicates specific characteristics. Accordingly, for example, a plurality of mutations are detected and the results thereof are judged comprehensively, which allows better diagnosis and treatment to be performed. Therefore, when the probe kit of the present invention is allowed to contain at least two types of probes of the present invention, mutations can be detected more easily for diagnoses, treatments, etc.

<Diagnostic Method>

A diagnostic method of the present invention is a method of diagnosing leukemia and is characterized by including a step of detecting a mutation in an abl gene by the mutation detection method of the present invention. In the present invention, it is characterized by detecting a mutation in an abl gene using the aforementioned probe of the present invention, and other steps and conditions are not limited at all.

According to the present invention, the resistance to a leukemia drug can be judged according to the presence or absence of a mutation at a specific site of the abl gene. Examples of the leukemia drug include imatinib and imatinib mesylate.

Next, the present invention is described using examples but is not limited by the following examples.

EXAMPLE 1

Point Mutation (A→G) at Base 730 in abl Gene

Probes of the present invention were used to carry out Tm analysis with respect to the point mutation (A→G) at base 730 in an abl gene.

The following plasmids were prepared: a plasmid (hereinafter referred to as "wtDNA") in which a normal abl gene sequence with no mutation in A at base 730 indicated in SEQ ID NO: 1 had been inserted, and a plasmid (hereinafter referred to as "mtDNA") in which a mutated abl gene (abl tyrosine kinase A730G, amino acid information M244V) with A at base 730 mutated into G had been inserted. Thereafter, both were prepared in a predetermined ratio (mtDNA: wtDNA=3:97) and 104 copy/test (1 µL) thereof was added to 49 µL of the following PCR reaction solution. Thus a PCR reaction was carried out. In the PCR reaction solution, the end concentration of the detection probe was 50 µM. In the PCR reaction, using a thermal cycler, after treating at 95° C. for 60 seconds, one cycle of treatment at 95° C. for 1 second and 58° C. for 30 seconds was repeated for 50 cycles, and further it was treated at 95° C. for 1 second and 40° C. for 60 seconds. Subsequently, the PCR reaction solution was heated from 40° C. to 95° C. at a rate of temperature climb of 1° C./3 seconds, and the change in fluorescence intensity over time was measured (with a wavelength of 585 to 700 nm).

TABLE 1

<PCR reaction solution; unit: µl>

| | |
|---|---|
| Distilled water | 25.25 |
| 10 × gene Taq buffer* | 5 |
| 40% Glycerol | 12.5 |
| 2.5 mM dNTPs | 4 |

TABLE 1-continued

<PCR reaction solution; unit: μl>

| | | |
|---|---|---|
| 100 μM sense primer | 1 (Example) | 0.5 (Comparative Example) |
| 100 μM antisense primer | 0.5 (Example) | 1 (Comparative Example) |
| 5 μM detection probe | 0.5 | |
| 5 U/μL Gene Taq FP* | 0.25 | |
| Total | 49 μL | |

*Trade name, Gene Taq Fp: manufactured by Nippon Gene Co., Ltd. (the same applies below)

```
            Sense primer
                                    SEQ ID NO: 17
            5'-gacaagtgggagatggaacgc-3'

Antisense primer
                                    SEQ ID NO: 18
            5'-cacggccaccgtcagg-3'
```

EXAMPLE 1-1

```
            Detection probe A1
                                    SEQ ID NO: 2
            5'-tgtgcttcaCggtgatgtcc-(TAMRA)-3'
```

EXAMPLE 1-2

```
            Detection probe A2
                                    SEQ ID NO: 3
            5'-gtgcttcaCggtgatgtccgtgcgttcc-(TAMRA)-3'
```

COMPARATIVE EXAMPLE 1

```
            Detection probe
                                    SEQ ID NO: 35
            5'-(TAMRA)-caccGtgaagcacaag-P-3'
```

These results are shown in FIG. 1. FIG. 1 shows graphs (melting curves) of Tm analysis that indicate the change in fluorescence intensity accompanying temperature rise (differential value=(−d fluorescence intensity increase/dt), the same applies below). In FIG. 1, (A) shows the result of Example 1-1, (B) the result of Example 1-2, and (C) the result of Comparative Example 1. When each probe and wtDNA (100%) as well as each probe and mtDNA (100%) were hybridized under the same conditions, respectively, the respective peaks were as follows and were used as evaluation criteria.

TABLE 2

| | Peak Temperature (° C.) | |
|---|---|---|
| Probe | wtDNA (100%) | mtDNA (100%) |
| Example 1-1 | 56.0 | 65.0 |
| Example 1-2 | 69.0 | 74.0 |
| Comparative Example 1 | 50.0 | 57.0 |

As shown in FIGS. 1(A) and (B), the use of the probes of Examples 1-1 and 1-2 resulted in detection of peaks (° C.) of wtDNA and mtDNA that were comparable to the evaluation criteria. On the other hand, as shown in FIG. 1(C), when the probe of Comparative Example 1 was used, the peak of mtDNA was not detected. This result proved that the probes of the present invention allowed the mtDNA detection sensitivity to improve even when mtDNA and wtDNA coexisted.

EXAMPLE 2

Point Mutation (G→A) at Base 749 in abl Gene

Probes of the present invention were used to carry out Tm analysis with respect to the point mutation (G→A) at base 749 in an abl gene.

The following plasmids were prepared: a plasmid (hereinafter referred to as "wtDNA") in which a normal abl gene sequence with no mutation in G at base 749 indicated in SEQ ID NO: 1 had been inserted, and a plasmid (hereinafter referred to as "mtDNA") in which a mutated abl gene (abl tyrosine kinase G749A (amino acid information G250E)) with G at base 749 mutated into A had been inserted. Thereafter, both were prepared in a predetermined ratio (mtDNA:wtDNA=3:97) and 104 copy/test (1 μL) thereof was added to 49 μL of the following PCR reaction solution. Thus a PCR reaction was carried out. The PCR reaction and detection of fluorescence intensity were carried out in the same manner as in Example 1.

TABLE 3

<PCR reaction solution; unit: μl>

| | | |
|---|---|---|
| Distilled water | 18.25 | |
| 10 × gene Taq buffer * | 5 | |
| 40% Glycerol | 18.75 | |
| 2.5 mM dNTPs | 4 | |
| 100 mM MgCl$_2$ | 0.75 | |
| 100 μM sense primer | 0.5 (Example) | 1 (Comparative Example) |
| 100 μM antisense primer | 1 (Example) | 0.5 (Comparative Example) |
| 5 μM detection probe | 0.5 | |
| 5 U/μL Gene Taq FP * | 0.25 | |
| Total | 49 μL | |

```
            Sense primer
                                    SEQ ID NO: 19
            5'-gacaagtgggagatggaacgc-3'

Antisense primer
                                    SEQ ID NO: 20
            5'-cacggccaccgtcagg-3'
```

EXAMPLE 2-1

```
            Detection probe B1
                                    SEQ ID NO: 4
            5'-(TAMRA)-caagctgggcgAgggcc-P-3'
```

EXAMPLE 2-21

```
            Detection probe B2
                                    SEQ ID NO: 5
            5'-(TAMRA)-cacaagctgggcgAggg-P-3'
```

COMPARATIVE EXAMPLE 21

```
Detection probe
                                   SEQ ID NO: 36
5'-(TAMRA)-cccTcgcccagctt-P-3'
```

Figure 2:
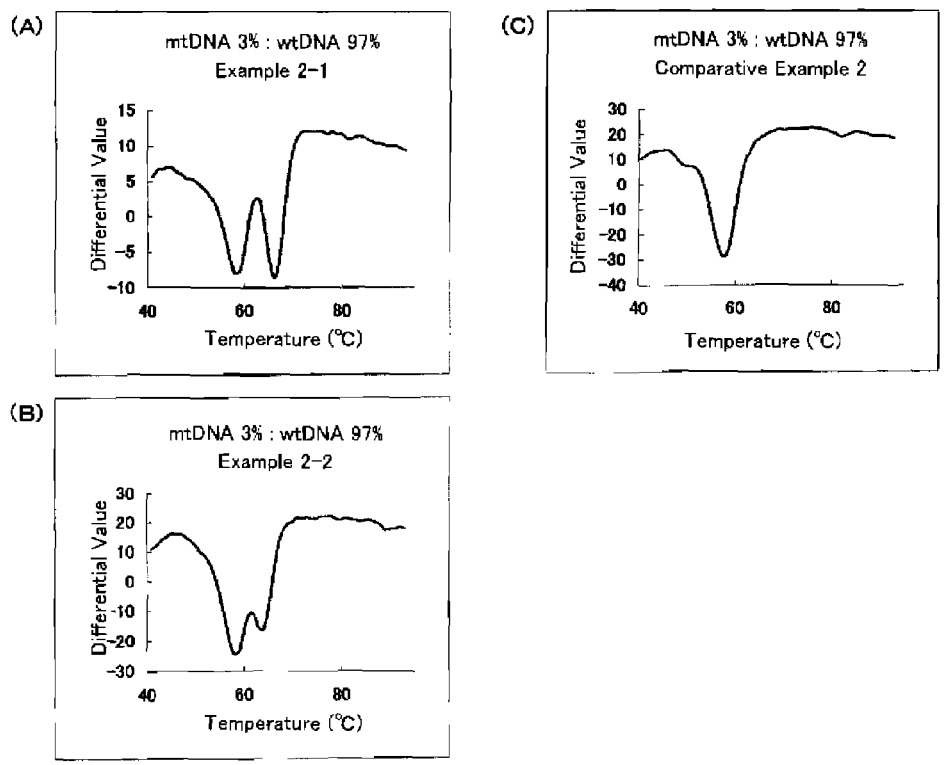
FIG. 2 shows graphs indicating the results of Tm analysis in another example of the present invention.

These results are shown in FIG. 2. FIG. 2 shows graphs of Tm analysis that indicate the change in fluorescence intensity accompanying temperature rise. In FIG. 2, (shows the result of Example 2-1, (B) the result of Example 2-2, and (C) the result of Comparative Example 2. When each probe and wtDNA (100%) as well as each probe and mtDNA (100%) were hybridized under the same conditions, respectively, the respective peaks were as follows and were used as evaluation criteria.

TABLE 4

|  | Peak Temperature (° C.) | |
|---|---|---|
| Probe | wtDNA (100%) | mtDNA (100%) |
| Example 2-1 | 59.0 | 66.0 |
| Example 2-2 | 58.0 | 64.0 |

As shown in FIGS. 2(A) and (B), the use of the probes of Examples 2-1 and 2-2 resulted in detection of peaks (° C.) of wtDNA and mtDNA that were comparable to the evaluation criteria. On the other hand, as shown in FIG. 2(C), when the probe of Comparative Example 2 was used, the peak of mtDNA was not detected. This result proved that the probes of the present invention allowed the mtDNA detection sensitivity to improve even when mtDNA and wtDNA coexisted.

EXAMPLE 3

Point Mutation (A→G) at Base 943 in abl Gene

Probes of the present invention were used to carry out Tm analysis with respect to the point mutation (A→U) at base 943 in an abl gene.

The following plasmids were prepared: a plasmid (hereinafter referred to as "wtDNA") in which a normal abl gene sequence with no mutation in A at base 943 indicated in SEQ ID NO: 1 had been inserted, and a plasmid (hereinafter referred to as "mtDNA") in which a mutated abl gene (abl tyrosine kinase A943G (amino acid information T315A)) with A at base 943 mutated into G had been inserted. Thereafter, both were prepared in a predetermined ratio (mtDNA:wtDNA=3:97) and $10^4$ copy/test (1 μL) thereof was added to 49 μL of the following PCR reaction solution. Thus a PCR reaction was carried out. The PCR reaction and detection of fluorescence intensity were carried out in the same manner as in Example 1.

TABLE 5

| <PCR reaction solution; unit: μl> | | |
|---|---|---|
| Distilled water | 31.5 | |
| 10 × gene Taq buffer * | 5 | |
| 40% Glycerol | 6.25 | |
| 2.5 mM dNTPs | 4 | |
| 100 μM sense primer | 1 (Example) | 0.5 (Comparative Example) |
| 100 μM antisense primer | 0.5 (Example) | 1 (Comparative Example) |
| 5 μM detection probe | 0.5 | |
| 5 U/μL Gene Taq FP * | 0.25 | |
| Total | 49 μL | |

```
Sense primer
                                   SEQ ID NO: 21
5'-ggacggacggaccgtcctcgttgtcttgttggc-3'

Antisense primer
                                   SEQ ID NO: 22
5'-ggacggacggaccgcactccctcaggtagtccag-3'
```

EXAMPLE 3-1

```
Detection probe C1
                                   SEQ ID NO: 6
5'-(Pacific Blue)-ctcagCgatgatatagaacgg-P-3'
```

EXAMPLE 3-2

```
Detection probe C2
                                   SEQ ID NO: 7
5'-(TAMRA)-cagCgatgatatagaacggg-P-3'
```

COMPARATIVE EXAMPLE 3-1

```
Detection probe C1
                                   SEQ ID NO:37
5'-(TAMRA)-catgaactcaGcgatgatatag-P-3'
```

COMPARATIVE EXAMPLE 3-2

```
Detection probe
                                   SEQ ID NO:38
5'-(TAMRA)-cccgttctatatcatcgCtg-P-3'
```

Figure 3:
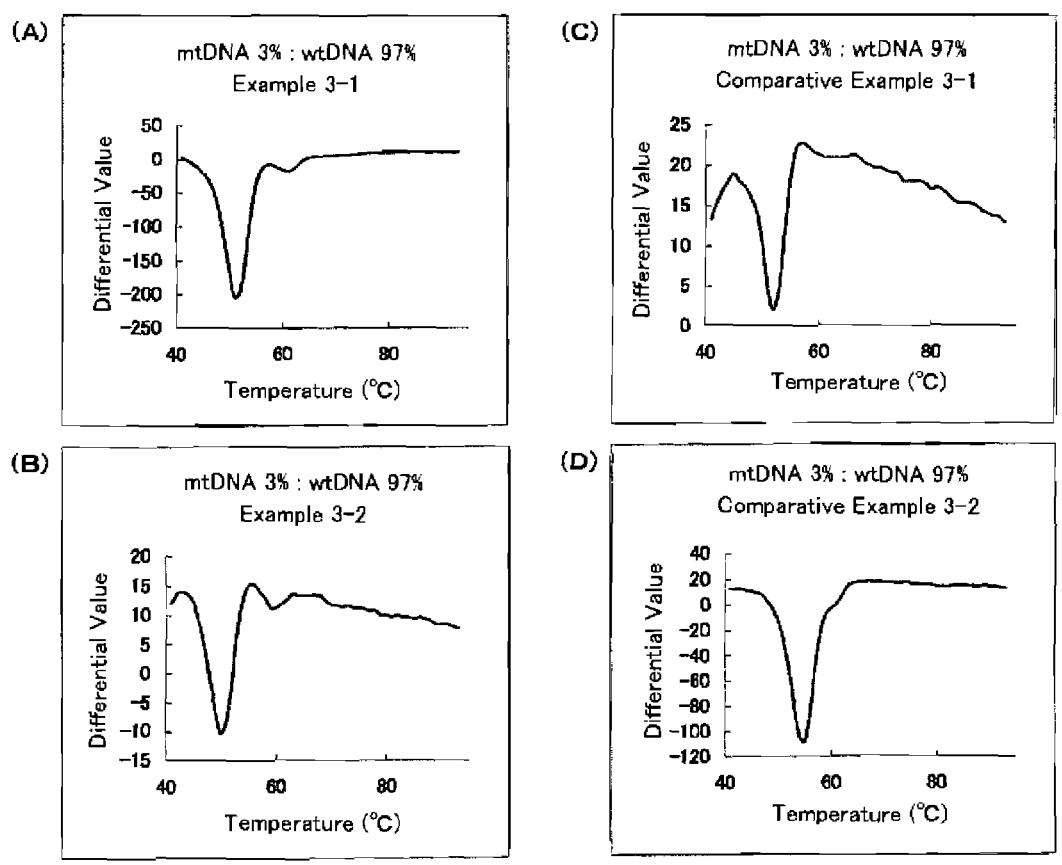
FIG. 3 shows graphs indicating the results of Tm analysis in still another example of the present invention.

These results are shown in FIG. 3. FIG. 3 shows graphs of Tm analysis that indicate the change in fluorescence intensity accompanying temperature rise. In FIG. 3, (A) shows the result of Example 3-1, (B) the result of Example 3-2, (C) the result of Comparative Example 3-1, and (D) the result of Comparative Example 3-2. When each probe and wtDNA (100%) as well as each probe and mtDNA (100%) were hybridized under the same conditions, respectively, the respective peaks were as follows and were used as evaluation criteria.

TABLE 6

|  | Peak Temperature (° C.) | |
|---|---|---|
| Probe | wtDNA (100%) | mtDNA (100%) |
| Example 3-1 | 52.0 | 61.0 |
| Example 3-2 | 50.0 | 60.0 |
| Comparative Example 3-1 | 52.0 | N.D |
| Comparative Example 3-2 | 55.0 | N.D |

As shown in FIGS. 3(A) and (B), the use of the probes of Examples 3-1 and 3-2 resulted in detection of peaks (° C.) of wtDNA and mtDNA that were comparable to the evaluation criteria. On the other hand, as shown in FIGS. 3(C) and (D), when the probes of Comparative Examples 3-1 and 3-2 were used, the peak of mtDNA was not detected. This result proved that the probes of the present invention allowed the mtDNA detection sensitivity to improve even when mtDNA and wtDNA coexisted.

EXAMPLE 4

Point Mutation (C→T) at Base 944 in abl Gene

Probes of the present invention were used to carry out Tm analysis with respect to the point mutation (C→T) at base 944 in an abl gene.

The following plasmids were prepared: a plasmid (hereinafter referred to as "wtDNA") in which a normal abl gene sequence with no mutation in C at base 944 indicated in SEQ ID NO: 1 had been inserted, and a plasmid (hereinafter referred to as "mtDNA") in which a mutated abl gene (abl tyrosine kinase C944T (amino acid information T315I)) with C at base 944 mutated into T had been inserted. Thereafter, both were prepared in a predetermined ratio (mtDNA:wtDNA=3:97) and 10⁴ copy/test (1 µL) thereof was added to 49 µL of the PCR reaction solution indicated in Table 3. Thus a PCR reaction was carried out. The PCR reaction and detection of fluorescence intensity were carried out in the same manner as in Example 1.

```
Sense primer
                                              SEQ ID NO:23
5'-ggacggacggaccgtcctcgttgtcttgttggc-3'

Antisense primer
                                              SEQ ID NO:24
5'-ggacggacggaccgcactccctcaggtagtccag-3'
```

EXAMPLE 4-1

```
Detection probe D1
                                              SEQ ID NO:8
5'(BODIPY FL)-ctcaAtgatgatatagaacg-P-3'
```

EXAMPLE 4-2

```
Detection probe D2
                                              SEQ ID NO:9
5'-actcaAtgatgatatagaac-(TAMRA)-3'
```

COMPARATIVE EXAMPLE 4-1

```
Detection probe
                                              SEQ ID NO:39
5'(TAMRA)-cccgttctatatcatcaTtgag-P-3'
```

COMPARATIVE EXAMPLE 4-2

```
Detection probe
                                              SEQ ID NO:40
5'-(TAMRA)-ccgttctatatcatcaTtg-P-3'
```

Figure 4:
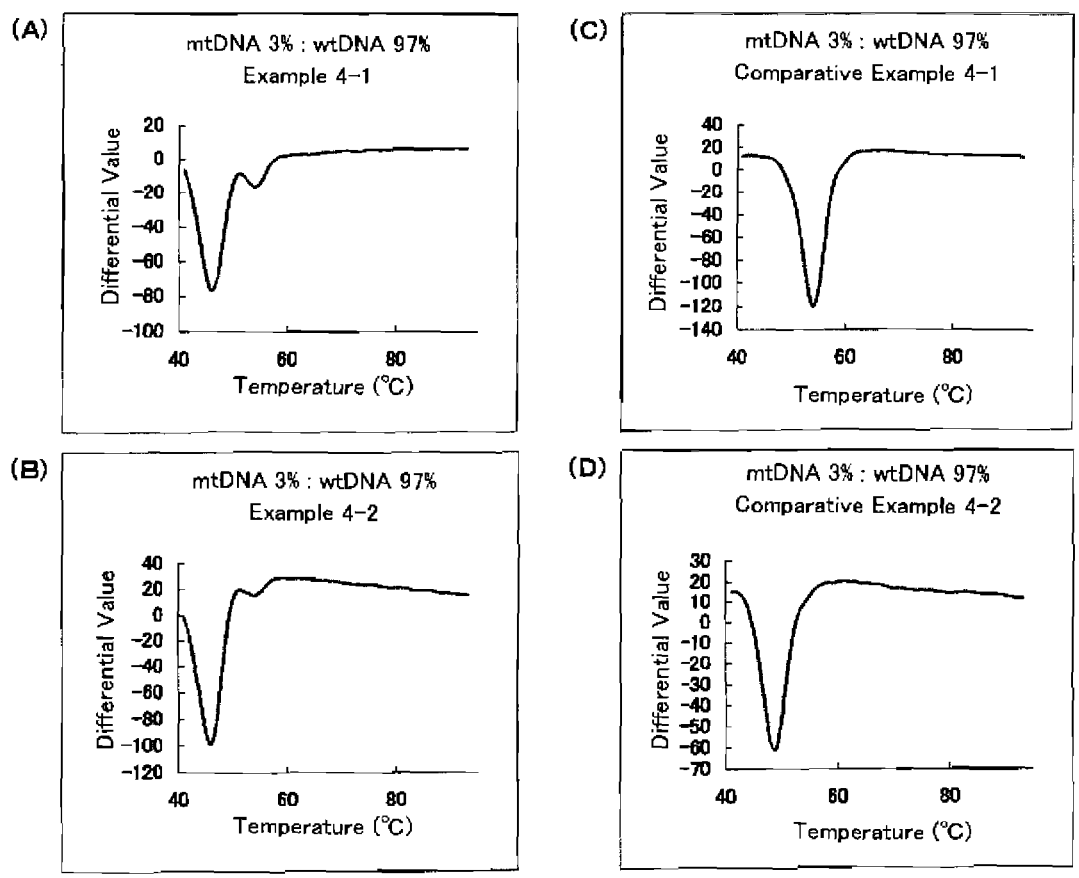
FIG. 4 shows graphs indicating the results of Tm analysis in yet another example of the present invention.

These results are shown in FIG. 4. FIG. 4 shows graphs of Tm analysis that indicate the change in fluorescence intensity accompanying temperature rise. In FIG. 4, (A) shows the result of Example 4-1, (B) the result of Example 4-2, (C) the result of Comparative Example 4-1, and (D) the result of Comparative Example 4-2. When each probe and wtDNA (100%) as well as each probe and mtDNA (100%) were hybridized under the same conditions, respectively, the respective peaks were as follows and were used as evaluation criteria.

TABLE 7

| | Peak Temperature (° C.) | |
|---|---|---|
| Probe | wtDNA (100%) | mtDNA (100%) |
| Example 4-1 | 46.0 | 55.0 |
| Example 4-2 | 46.0 | 55.0 |
| Comparative Example 4-1 | 54.0 | 59.0 |
| Comparative Example 4-2 | 49.0 | 54.0 |

As shown in FIGS. 4(A) and (B), the use of the probes of Examples 4-1 and 4-2 resulted in detection of peaks (° C.) of wtDNA and mtDNA that were comparable to the evaluation criteria. On the other hand, as shown in FIGS. 4(C) and (D), when the probes of Comparative Examples 4-1 and 4-2 were used, the peak of mtDNA was not detected. This result proved that the probes of the present invention allowed the mtDNA detection sensitivity to improve even when mtDNA and wtDNA coexisted.

EXAMPLE 5

Point Mutation (C→G) at Base 951 in abl Gene

A probe of the present invention was used to carry out Tm analysis with respect to the point mutation (C→G) at base 951 in an abl gene.

The following plasmids were prepared: a plasmid (hereinafter referred to as "wtDNA") in which a normal abl gene sequence with no mutation in C at base 951 indicated in SEQ ID NO: 1 had been inserted, and a plasmid (hereinafter referred to as "mtDNA") in which a mutated abl gene (abl tyrosine kinase C951G (amino acid information F317L)) with C at base 951 mutated into G had been inserted. Thereafter, both were prepared in a predetermined ratio (mtDNA: wtDNA=3:97) and 10⁴ copy/test (1 µL) thereof was added to 49 µL of the PCR reaction solution indicated in Table 3. Thus a PCR reaction was carried out. The PCR reaction and detection of fluorescence intensity were carried out in the same manner as in Example 1.

```
Sense primer
                                              SEQ ID NO:25
5'-ggacggacggaccgtcctcgttgtcttgttggc-3'

Antisense primer
                                              SEQ ID NO:26
5'-ggacggacggaccgcactccctcaggtagtccag-3'
```

EXAMPLE 5

Detection probe E1
SEQ ID NO:10
5'-ttcccgtaggtcatCaac-(TAMRA)-3'

COMPARATIVE EXAMPLE 5-1

Detection probe
SEQ ID NO:41
5'-ttGatgacctacgggaacc-(TAMRA)-3'

COMPARATIVE EXAMPLE 5-2

Detection probe
SEQ ID NO:42
5'-ttGatgacctacgggaac-(TAMRA)-3'

COMPARATIVE EXAMPLE 5-3

Detection probe
SEQ ID NO:43
5'-(TAMRA)-cccgtaggtcatCaactc-P-3'

Figure 5:
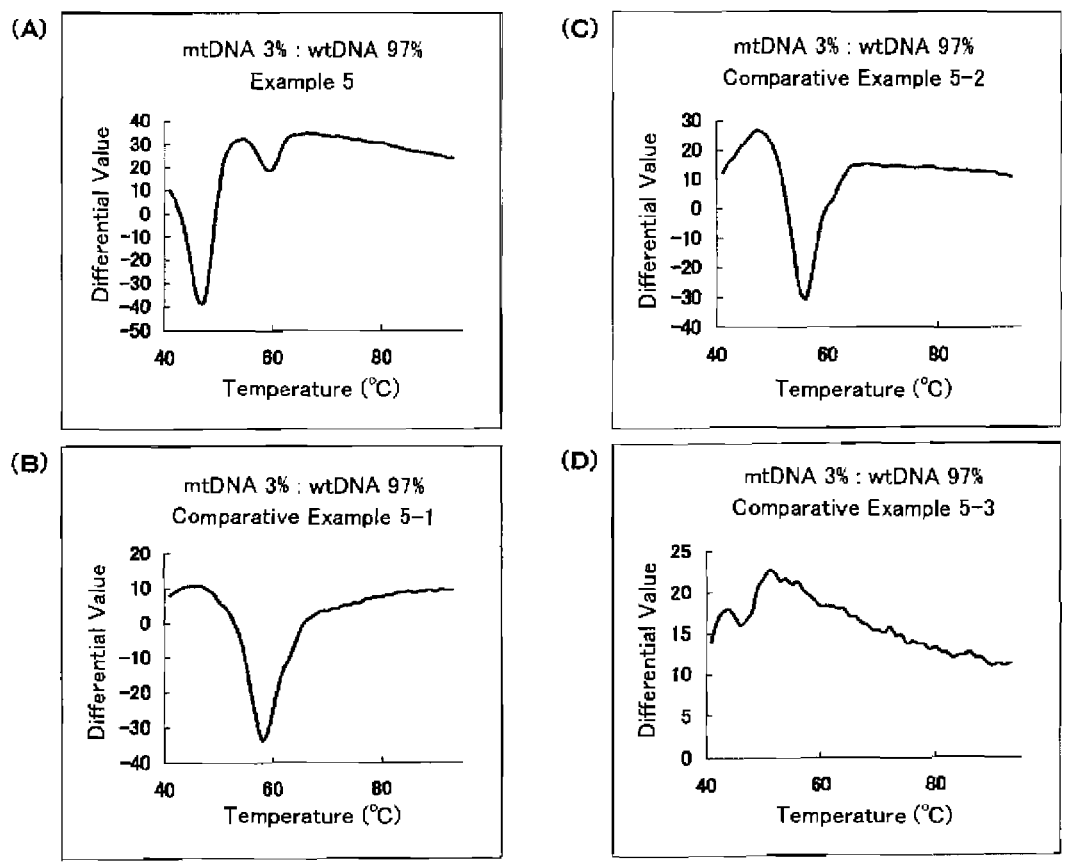
FIG. 5 shows graphs indicating the results of Tm analysis in a further example of the present invention.

These results are shown in FIG. 5. FIG. 5 shows graphs of Tm analysis that indicate the change in fluorescence intensity accompanying temperature rise. In FIG. 5, (A) shows the result of Example 5, (B) the result of Comparative Example 5-1, (C) the result of Comparative Example 5-2, and (D) the result of Comparative Example 5-3. When each probe and wtDNA (100%) as well as each probe and mtDNA (100%) were hybridized under the same conditions, respectively, the respective peaks were as follows and were used as evaluation criteria.

TABLE 8

| | Peak Temperature (° C.) | |
|---|---|---|
| Probe | wtDNA (100%) | mtDNA (100%) |
| Example 5 | 47.0 | 60.0 |
| Comparative Example 5-1 | 58.0 | 62.0 |
| Comparative Example 5-2 | 56.0 | 60.0 |
| Comparative Example 5-3 | N.D. | N.D. |

As shown in FIG. 5(A), the use of the probe of Example 5 resulted in detection of peaks (0° C.) of wtDNA and mtDNA that were comparable to the evaluation criteria. On the other hand, as shown in FIGS. 5(B) and (C), when the probes of Comparative Examples 5-1 and 5-2 were used, the peak of mtDNA was not detected. Furthermore, as shown in FIG. 5(D), when the probe of Comparative Example 5-3 was used, a large number of peaks were present and were not discriminative. This result proved that the probe of the present invention allowed the mtDNA detection sensitivity to improve even when mtDNA and wtDNA coexisted.

EXAMPLE 6

Point Mutation (T→C) at Base 1052 in abl Gene

A probe of the present invention was used to carry out Tm analysis with respect to the point mutation (T→C) at base 1052 in an abl gene.

The following plasmids were prepared: a plasmid (hereinafter referred to as "wtDNA") in which a normal abl gene sequence with no mutation in T at base 1052 indicated in SEQ ID NO: 1 had been inserted, and a plasmid (hereinafter referred to as "mtDNA") in which a mutated abl gene (abl tyrosine kinase T1052C (amino acid information M351T)) with T at base 1052 mutated into C had been inserted. Thereafter, both were prepared in a predetermined ratio (mtDNA:wtDNA=3:97) and $10^4$ copy/test (1 µL) thereof was added to 49 µL of the PCR reaction solution indicated in Table 1. Thus a PCR reaction was carried out. The PCR reaction and detection of fluorescence intensity were carried out in the same manner as in Example 1.

Sense primer
SEQ ID NO:27
5'-ggccggccccgtggtgctgctgtacatg-3'

Antisense primer
SEQ ID NO:28
5'-cacgccctgtgactccatg-3'

EXAMPLE 6

Detection probe F1
SEQ ID NO:11
5'-gtcagccaCggagtacc-(BODIPY FL)-3'

COMPARATIVE EXAMPLE 6-1

Detection probe
SEQ ID NO:44
5'-ccactcagatctcgtcagccaCggagtacc-(TAMRA)-3'

COMPARATIVE EXAMPLE 6-2

Detection probe
SEQ ID NO: 45
5'-(TAMRA)-ccaTggagtacctagCgaag-P-3'

Figure 6:
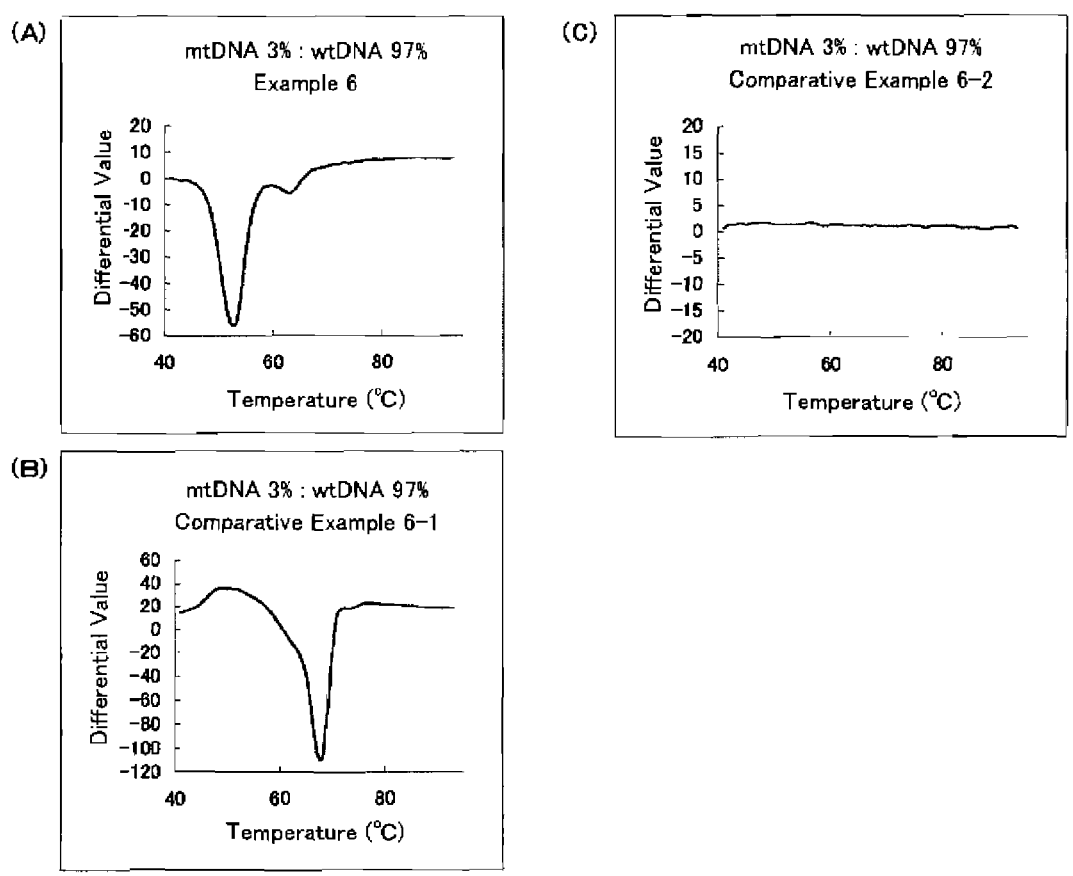
FIG. 6 shows graphs indicating the results of Tm analysis in still another example of the present invention.

These results are shown in FIG. 6. FIG. 6 shows graphs of Tm analysis that indicate the change in fluorescence intensity accompanying temperature rise. In FIG. 6, (A) shows the result of Example 6, (B) the result of Comparative Example 6-1, and (C) the result of Comparative Example 6-2. When each probe and wtDNA (100%) as well as each probe and mtDNA (100%) were hybridized under the same conditions, respectively, the respective peaks were as follows and were used as evaluation criteria.

TABLE 9

| | Peak Temperature (° C.) | |
|---|---|---|
| Probe | wtDNA (100%) | mtDNA (100%) |
| Example 6 | 53.0 | 64.0 |
| Comparative Example 6-1 | 68.0 | 73.0 |
| Comparative Example 6-2 | N.D. | N.D. |

As shown in FIG. 6(A), the use of the probe of Example 6 resulted in detection of peaks (° C.) of wtDNA and mtDNA that were comparable to the evaluation criteria. On the other hand, as shown in FIGS. 6(B) and (C), when the probes of Comparative Examples 6-1 and 6-2 were used, the peak of mtDNA was not detected. This result proved that the probe of the present invention allowed the mtDNA detection sensitivity to improve even when mtDNA and wtDNA coexisted.

EXAMPLE 7

Point Mutation (A→G) at Base 1064 in abl Gene

The following plasmids were prepared: a plasmid (hereinafter referred to as "wtDNA") in which a normal abl gene sequence with no mutation in A at base 1064 indicated in SEQ ID NO: 1 had been inserted, and a plasmid (hereinafter referred to as "mtDNA") in which a mutated abl gene (abl tyrosine kinase A1064G (amino acid information E355G)) with A at base 1064 mutated into G had been inserted. Thereafter, both were prepared in a predetermined ratio (mtDNA : wtDNA =3:97) and $10^4$ copy/test (1µL) thereof was added to 49 µL of the following PCR reaction solution. Thus a PCR reaction was carried out. The PCR reaction and detection of fluorescence intensity were carried out in the same manner as in Example 1.

TABLE 10

| <PCR reaction solution; unit: µl> | |
| --- | --- |
| Distilled water | 28.375 |
| 10 × gene Taq buffer * | 5 |
| 40% Glycerol | 9.375 |
| 2.5 mM dNTPs | 4 |
| 100 µM sense primer | 1 |
| 100 µM antisense primer | 0.5 |
| 5 µM detection probe | 0.5 |
| 5 U/µL Gene Taq FP * | 0.25 |
| Total | 49 µL |

```
Sense primer
                                     SEQ ID NO: 29
5'-ggccggccccgtggtgctgctgtacatg-3'

Antisense primer
                                     SEQ ID NO: 30
5'-cacgccctgtgactccatg-3'
```

EXAMPLE 7-1

```
Detection probe G1
                                     SEQ ID NO: 12
5'-gtttttcttcCccaggtactc-(TAMRA)-3'
```

EXAMPLE 7-2

```
Detection probe G2
                                     SEQ ID NO: 13
5'-gtttttcttcCccaggtactcc-(TAMRA)-3'
```

COMPARATIVE EXAMPLE 7

```
Detection probe
                                     SEQ ID NO: 46
5'-(TAMRA)-cttcCccaggtactcc-P-3'
```

Figure 7:
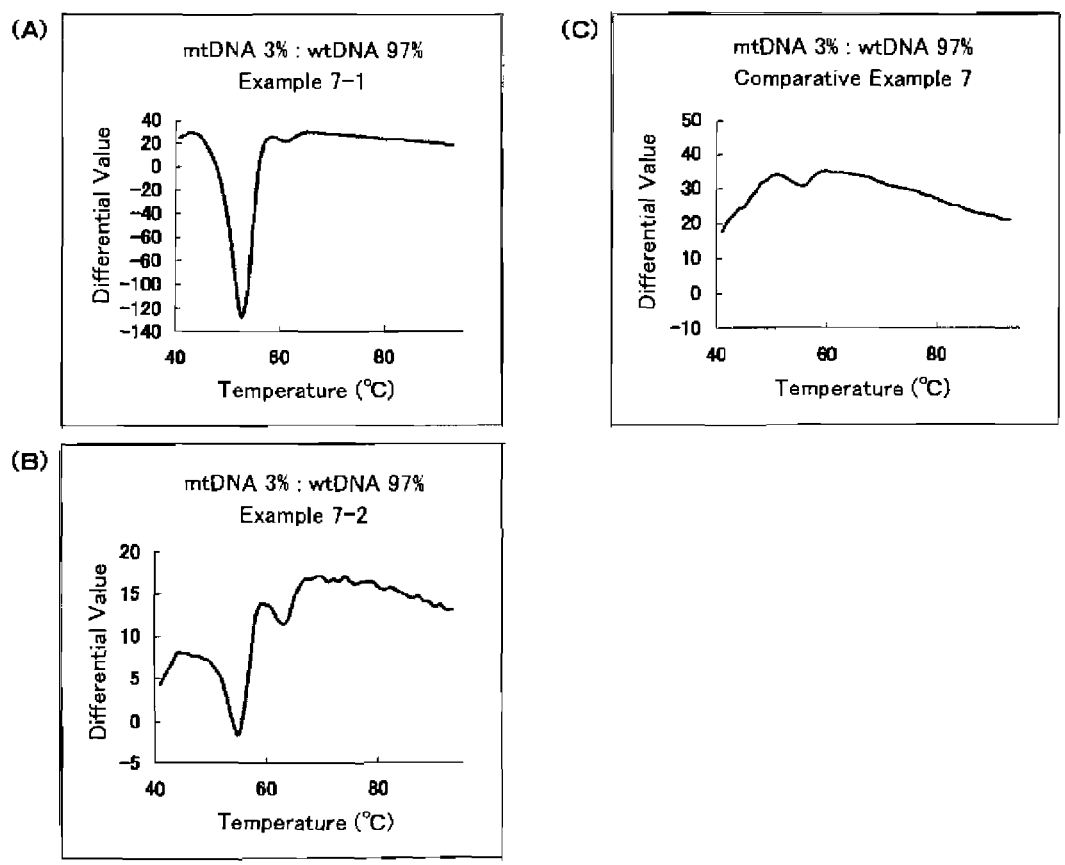
FIG. 7 shows graphs indicating the results of Tm analysis in yet another example of the present invention.

These results are shown in FIG. 7. FIG. 7 shows graphs of Tm analysis that indicate the change in fluorescence intensity accompanying temperature rise. In FIG. 7, (A) shows the result of Example 7-1, (B) the result of Example 7-2, and (C) the result of Comparative Example 7. When each probe and wtDNA (100%) as well as each probe and mtDNA (100%) were hybridized under the same conditions, respectively, the respective peaks were as follows and were used as evaluation criteria.

TABLE 11

| | Peak Temperature (° C.) | |
| --- | --- | --- |
| Probe | wtDNA (100%) | mtDNA (100%) |
| Example 7-1 | 53.0 | 62.0 |
| Example 7-2 | 55.0 | 63.0 |

As shown in FIGS. 7(A) and (B), the use of the probes of Examples 7-1 and 7-2 resulted in detection of peaks (° C.) of wtDNA and mtDNA that were comparable to the evaluation criteria. On the other hand, as shown in FIG. 7(C), when the probe of Comparative Example 7 was used, the peak of mtDNA was not detected. This result proved that the probes of the present invention allowed the mtDNA detection sensitivity to improve even when mtDNA and wtDNA coexisted.

EXAMPLE 8

Point Mutation (T→G) at Base 1075 in abl Gene

Probes of the present invention were used to carry out Tm analysis with respect to the point mutation (T→G) at base 1075 in an abl gene.

The following plasmids were prepared: a plasmid (hereinafter referred to as "wtDNA") in which a normal abl gene sequence with no mutation in T at base1075 indicated in SEQ ID NO: 1 had been inserted, and a plasmid (hereinafter referred to as "mtDNA") in which a mutated abl gene (abl tyrosine kinase T1075G (amino acid information F359V)) with T at base 1075 mutated into G had been inserted. Thereafter, both were prepared in a predetermined ratio (mtDNA: wtDNA=3:97) and 104 copy/test (1 µL) thereof was added to 49 µL of the PCR reaction solution indicated in Table 4. Thus a PCR reaction was carried out. The PCR reaction and detection of fluorescence intensity were carried out in the same manner as in Example 1.

```
Sense primer
                                     SEQ ID NO: 31
5'-ggccggccccgtggtgctgctgtacatg-3'

Antisense primer
                                     SEQ ID NO: 32
5'-cacgccctgtgactccatg-3'
```

EXAMPLE 8-1

```
Detection probe H1
                                      SEQ ID NO: 14
5'-gatgaCgtttttcttctcc-(TAMRA)-3'
```

EXAMPLE 8-2

```
Detection probe H2
                                      SEQ ID NO: 15
5'-tgtggatgaCgttttcttc-(TAMRA)-3'
```

COMPARATIVE EXAMPLE 8-1

```
Detection probe
                                      SEQ ID NO: 47
5'-(TAMRA)-ctgtggatgaCgtttttc-P-3'
```

COMPARATIVE EXAMPLE 8-2

```
Detection probe
                                      SEQ ID NO: 48
5'-(TAMRA)-cctgtggatgaCgttttc-P-3'
```

Figure 8:
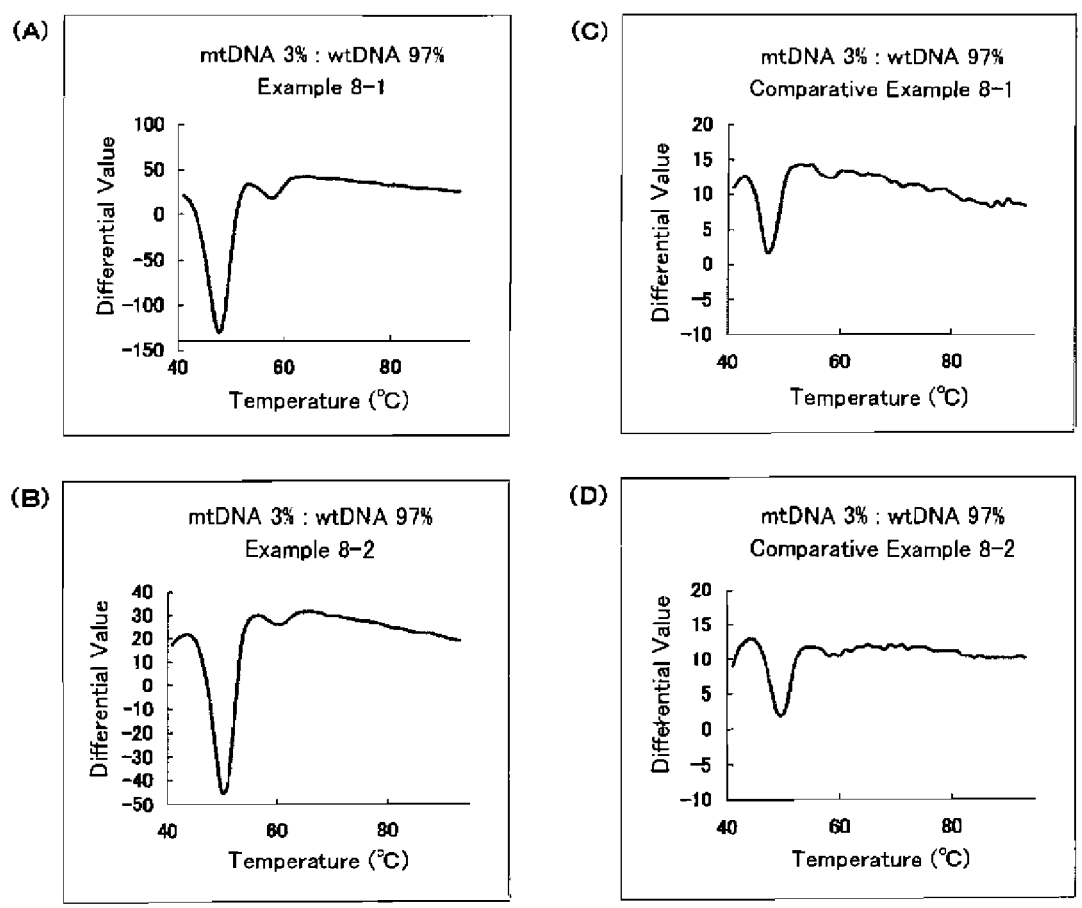
FIG. 8 shows graphs indicating the results of Tm analysis in a further example of the present invention.

These results are shown in FIG. 8. FIG. 8 shows graphs of Tm analysis that indicate the change in fluorescence intensity accompanying temperature rise. In FIG. 8, (A) shows the result of Example 8-1, (B) the result of Example 8-2, (C) the result of Comparative Example 8-1, and (D) the result of Comparative Example 8-2. When each probe and wtDNA (100%) as well as each probe and mtDNA (100%) were hybridized under the same conditions, respectively, the respective peaks were as follows and were used as evaluation criteria.

TABLE 12

| Probe | Peak Temperature (° C.) | |
|---|---|---|
| | wtDNA (100%) | mtDNA (100%) |
| Example 8-1 | 48.0 | 58.0 |
| Example 8-2 | 50.0 | 60.0 |
| Comparative Example 8-1 | 48.0 | 58.0 |
| Comparative Example 8-2 | 50.0 | 59.0 |

As shown in FIGS. 8(A) and (B), the use of the probes of Examples 8-1 and 8-2 resulted in detection of peaks (° C.) of wtDNA and mtDNA that were comparable to the evaluation criteria. On the other hand, as shown in FIGS. 8(C) and (D), when the probes of Comparative Examples 8-1 and 8-2 were used, a large number of peaks appeared and the peak of mtDNA was not discriminative. This result proved that the probes of the present invention allowed the mtDNA detection sensitivity to improve even when mtDNA and wtDNA coexisted.

EXAMPLE 9

Point Mutation (A→G) at Base 1187 in abl Gene

A probe of the present invention was used to carry out Tm analysis with respect to the point mutation (A→G) at base 1187 in an abl gene.

The following plasmids were prepared: a plasmid (hereinafter referred to as "wtDNA") in which a normal abl gene sequence with no mutation in A at base 1187 indicated in SEQ ID NO: 1 had been inserted, and a plasmid (hereinafter referred to as "mtDNA") in which a mutated abl gene (abl tyrosine kinase A1187G (amino acid information H396R)) with A at base 1187 mutated into G had been inserted. Thereafter, both were prepared in a predetermined ratio (mtDNA : wtDNA =3:97) and $10^4$ copy/test (1 μL) thereof was added to 49 μL of the following PCR reaction solution. Thus a PCR reaction was carried out. The PCR reaction and detection of fluorescence intensity were carried out in the same manner as in Example 1.

TABLE 13

| <PCR reaction solution; unit: μl> | |
|---|---|
| Distilled water | 31.5 |
| 10 × gene Taq buffer * | 5 |
| 40% Glycerol | 6.25 |
| 2.5 mM dNTPs | 4 |
| 100 μM sense primer | 0.5 |
| 100 μM antisense primer | 0.5 |
| 5 μM detection probe | 0.5 |
| 5 U/μL Gene Taq FP * | 0.25 |
| Total | 49 μL |

```
Sense primer
                                      SEQ ID NO: 33
5'-acctacctacctagatcttgctgcccgaaactg-3'

Antisense primer
                                      SEQ ID NO: 34
5'-acctacctacctcttgttgtaggccaggctctc-3'
```

EXAMPLE 9

```
Detection probe I1
                                      SEQ ID NO: 16
5'-ccagcaCgggctgtgtaggtgtcc-(TAMRA)-3'
```

COMPARATIVE EXAMPLE 9-1

```
Detection probe
                                      SEQ ID NO: 49
5'-gctccagcaCgggctgtgtaggtgtcc-(TAMRA)-3'
```

COMPARATIVE EXAMPLE 9-2

```
Detection probe
                                      SEQ ID NO: 50
5'-(TAMRA)-ccagcaCgggctgtgtag-P-3'
```

Figure 9:
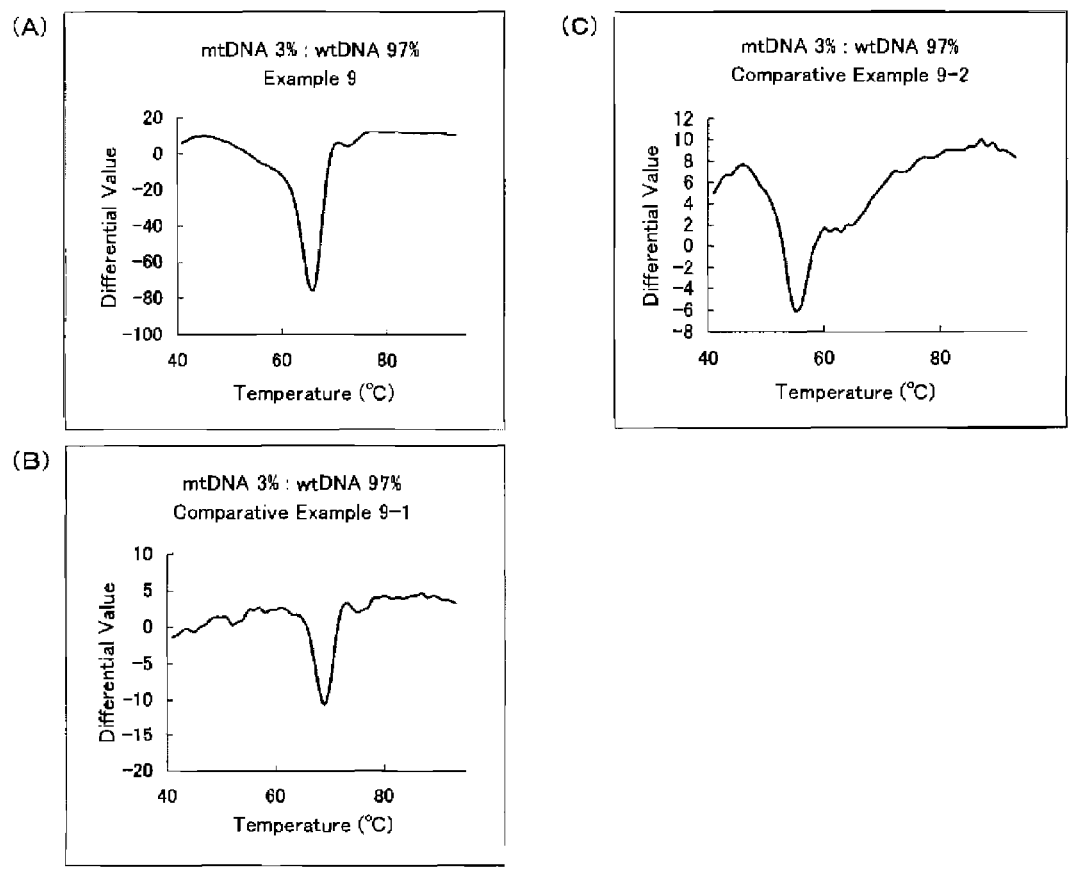
FIG. 9 shows graphs indicating the results of Tm analysis in still another example of the present invention.

These results are shown in FIG. 9. FIG. 9 shows graphs of Tm analysis that indicate the change in fluorescence intensity accompanying temperature rise. In FIG. 9, (A) shows the result of Example 9, (B) the result of Comparative Example 9-1, and (C) the result of Comparative Example 9-2. When each probe and wtDNA (100%) as well as each probe and mtDNA (100%) were hybridized under the same conditions, respectively, the respective peaks were as follows and were used as evaluation criteria.

TABLE 14

| Probe | Peak Temperature (° C.) | |
|---|---|---|
| | wtDNA (100%) | mtDNA (100%) |
| Example 9 | 66.0 | 73.0 |
| Comparative Example 9-1 | 69.0 | 75.0 |
| Comparative Example 9-2 | 55.0 | 65.0 |

As shown in FIG. 9(A), the use of the probe of Example 9 resulted in detection of peaks (° C.) of wtDNA and mtDNA that were comparable to the evaluation criteria. On the other hand, as shown in FIGS. 9(B) and (C), when the probes of Comparative Examples 9-1 and 9-2 were used, a large number of peaks appeared and the peak of mtDNA was not discriminative. This result proved that the probe of the present invention allowed the mtDNA detection sensitivity to improve even when mtDNA and wtDNA coexisted.

INDUSTRIAL APPLICABILITY

As described above, even when an abl gene (mutated gene) in which a target mutation to be detected has occurred coexists with an abl gene (normal gene) in which no mutation has occurred, the probes of the present invention allow the target mutated gene to be detected. For instance, in the Tm analysis, since a conventional probe hybridizes to both a normal gene and a mutated gene, which are different only in a single base from each other as described above, the signals from both overlap in the melting curve and thereby it is very difficult to detect the presence of the mutated gene. On the other hand, although the probes of the present invention each hybridize to both a normal gene and a mutated gene, the signals from both can be separated in the melting curve. Thus, the present invention makes it possible to detect mutated genes, for example, even by the Tm analysis.

[Sequence Table]
TF08004-01.5T25.txt

---

The invention claimed is:

1. A probe composition comprising
   (i) a first probe comprising a fluorescent dye covalently bonded to (D1) oligonucleotide consisting of the base sequence of SEQ ID NO: 8,
   (ii) a second probe comprising a fluorescent dye covalently bonded to (D2) oligonucleotide consisting of the base sequence of SEQ ID NO: 9, or
   (iii) the first probe and the second probe.

2. The probe composition according to claim 1, wherein each of the first and second probes detects a mutation (C→T) of C at base 944 in the base sequence of SEQ ID NO: 1.

3. The probe composition according to claim 1, wherein each of the probes exhibits a signal independent of hybridization but does not exhibit a signal after hybridization to a target nucleic acid or each of the probes does not exhibit a signal when not hybridized to a target nucleic acid but exhibits a signal after hybridization to a target nucleic acid.

4. The probe composition according to claim 1, wherein each of the probes exhibits fluorescence when not hybridized to a target nucleic acid and a decrease in fluorescence after hybridization to a target nucleic acid.

5. The probe composition according to claim 4, wherein each of the probes has the fluorescent dye at a 5' end or 3' end of the oligonucleotides (D1) and (D2).

6. The probe composition according to claim 1, wherein the probe composition is a probe composition for melting temperature (Tm) analysis.

7. The probe composition according to claim 1, wherein the probe composition comprises the first probe.

8. The probe composition according to claim 1, wherein the probe composition comprises the second probe.

9. The probe composition according to claim 1, wherein the probe composition comprises the first probe and the second probe.

10. The probe composition according to claim 1, wherein the fluorescent dyes are covalently bonded to the 5' end of the oligonucleotides (D1) and (D2).

11. The probe composition according to claim 1, wherein the fluorescent dyes are covalently bonded to the 3' end of the oligonucleotides (D1) and (D2).

12. The probe composition according to claim 1, wherein the fluorescent dye is selected from the group consisting of fluorescein, phosphor, rhodamine, and polymethine dye.

* * * * *